United States Patent
Malek et al.

(10) Patent No.: US 6,498,024 B1
(45) Date of Patent: *Dec. 24, 2002

(54) SUBTRACTIVE AMPLIFICATION KIT USEFUL IN THE DIAGNOSIS OF GENETIC DISEASE MUTATION OR VARIATION

(75) Inventors: Lawrence T. Malek, Brampton (CA); Roy R. Sooknanan, Toronto (CA)

(73) Assignee: SignalGene Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/171,755

(22) PCT Filed: Apr. 29, 1997

(86) PCT No.: PCT/US97/07253

§ 371 (c)(1),
(2), (4) Date: Mar. 18, 1999

(87) PCT Pub. No.: WO97/41260

PCT Pub. Date: Nov. 6, 1997

Related U.S. Application Data

(63) Continuation-in-part of application No. 08/639,763, filed on Apr. 29, 1996, now Pat. No. 5,712,127.

(51) Int. Cl.⁷ .............................................. C12P 19/34

(52) U.S. Cl. ................. 435/91.21; 435/91.2; 435/91.51

(58) Field of Search ........................... 435/91.1, 91.51, 435/91.2, 91.21, 810; 536/24.33

(56) References Cited

U.S. PATENT DOCUMENTS

| | | | |
|---|---|---|---|
| 4,683,202 A | 7/1987 | Mullis | 435/91 |
| 4,889,818 A | 12/1989 | Gelfand et al. | 435/194 |
| 5,130,238 A | 7/1992 | Malek et al. | 435/91 |
| 5,409,818 A | 4/1995 | Davey et al. | 435/91.21 |
| 5,436,142 A | 7/1995 | Wigler et al. | 435/91.2 |
| 5,455,166 A | 10/1995 | Walker | 435/91.2 |
| 5,459,055 A | 10/1995 | Jendrisak et al. | 435/199 |
| 5,466,586 A | 11/1995 | Davey et al. | 435/91.21 |
| 5,503,979 A | 4/1996 | Kramer et al. | 435/6 |
| 5,545,522 A | 8/1996 | Van Gelder et al. | 435/6 |
| 5,554,517 A | 9/1996 | Davey et al. | 435/91.21 |

FOREIGN PATENT DOCUMENTS

WO    WO 96/02668    1/1996    ............ C12Q/1/68

OTHER PUBLICATIONS

Fahy, et al., "Self–sustained sequence replication (3SR):An Isothermal Transcription–based Amplification System Alternative to PCR", *PCR Methods and Applications*, pp. 25–33, (1991).

Hubank, et al., "Identifying differences in mRNA expression by representational difference analysis of cDNA", *Nucleic Acids Research*, vol. 22, No. 25, pp. 5640–5648, (1994).

Kuze, et al., "A new vector and RNase H method for the subtractive hybridization", *Nucleic Acids Research*, vol. 17, No. 2, pp. 807, (1989).

Lamar, et al., "Y–Encoded, Species–Specific DNA in Mice: Evidence That the Y Chromosome Exists in Two Polymorphic Forms in Inbred Strains", *Cells*, vol. 37, pp. 171–177, (1984).

Lisitsyn, et al., "Cloning the Differences Between Two Complex Gnomes", *Science*, pp. 946–951, (1993).

Mullis, et al., "Specific Enzymatic Amplification of DNA In Vitro: The Polymerase Chain Reaction", *Cold Spring Harbor Symp. Quant. Biol.*, vol. 51, pp. 263–273, (1986).

Myers, et al., "Reverse Transcription an dDNA Amplification by a Thermus thermophilus DNA Polymerase", *Biochemistry*, vol. 30:31, pp. 7661–7666, (1991).

Rosen, et al., "Subtractive Hybridization: A Technique for Isolation of Differentially Expressed Genes", *Toxicology Methods*, vol. 4, No. 2, pp. 135–147, (1994).

Saiki, "The Design and Optimization of the PCR", *Toxicol. Method.*, vol. 4, pp. 135–147, (1994).

Sambrook, et al., "Dot and Slot Hybridization of RNA", *Molecular Cloning: A Laboratory Manual*, pp. 7.53–7.55, (1989).

Sooknanan, et al., "Detection and direct sequence identification of BCR–ABL mRNA in Ph⁺ chronic myeloid leukemia", *Experimental Hematology*, vol. 21, pp. 1719–1724, (1993).

Sooknanan, et al., "Nucleic Acid Sequence–Based Amplification", *Molecular Methods for Virus Detection*, pp. 261–285 (1995).

Walker, et al., "A Chemiluminescent DNA Probe Test Based on Strand Displacement Amplification", *Molecular Methods for virus Detection*, pp. 329–349, (1995).

Wieland, et al., "A method for difference cloning: Gene amplification following subtractive hybridization", *Proc. Natl., Acad. Sci. USA*, vol. 87, pp. 2720–2724, (1990).

Yang, et al., "Cloning Differentially Expressed Genes", *Analytical Biochem.*, vol. 237, 109–114, (1996).

Zeng, et al., "Differential cDNA cloning by enzymatic degrading subtraction (EDS)", *Nucleic Acids Research*, vol., 22, No. 21, pp. 4381–4285, (1994).

(List continued on next page.)

*Primary Examiner*—Kenneth R. Horlick
(74) *Attorney, Agent, or Firm*—Fulbright & Jaworski

(57) ABSTRACT

A kit is provided for preferentially amplifying target RNA in a sample of tester RNA relative to non-target RNA in the sample, the kit driver sequences complementary to the non-target tester RNA under conditions where the driver sequences hybridize to the non-target RNA, a nucleic acid primer capable of hybridizing to the target RNA under conditions suitable for extension of the nucleic acid primer; and a promoter template capable of hybridizing to a DNA that is complementary to the target RNA under conditions suitable for extension of the complementary DNA such that a functional double promoter is formed.

11 Claims, 9 Drawing Sheets

OTHER PUBLICATIONS

PCR–Select cDNA subtraction kit, *CLONTECHniques,* vol. 10, No. 4, pp. 1–5, (1995).

Lopez–Fernandez, L.A. et al., "Construction of Subtractive cDNA Libraries from Limited Amounts of mRNA and Multiple Cycles of Subtraction", *BioTechniques*, vol. 15, No. 4, Oct. 1, 1993, pp. 654, 656, 658–659.

Palazzolo et al. (1990) *Gene*, vol. 88, pp. 25–36.

Rothstein et al. (1993) *Methods in Enzymology*, vol. 225, pp. 587–610.

Kreig and Melton (1987) *Methods in Enzymology*, vol. 155, pp. 397–415.

Wyatt et al. (1991) *BioTechniques*, vol. 11, pp. 764–769.

Sive and St. John, "A simple subtractive hybridization technique employing photoactivatable biotin and phenol extraction," *Nucleic Acids Research*, 16(22):10937–10938, 1988.

I.

II.

I.

II.

I.

II.

I.

II.

I.

II.

I.

II.

I.

p6-M (436 nt)
p5-G (105 nt)

II.

p6-M (436 nt)
p5-G (105 nt)

I.

II.

SUBTRACTIVE AMPLIFICATION KIT USEFUL IN THE DIAGNOSIS OF GENETIC DISEASE MUTATION OR VARIATION

The present application claims the benefit of priority to international application number PCT/US/97/07253 filed Apr. 29, 1997 and is a continuation-in-part U.S. application Ser. No. 08/639,763 filed Apr. 29, 1996, now issued as U.S. Pat. No. 5,712,127.

FIELD OF THE INVENTION

This invention relates to a method for selectively amplifying target RNA relative to non-target RNA in a sample of tester RNA.

BACKGROUND OF THE INVENTION

Disease is a deviation from the normal functioning of the body's organs or systems. This deviation can arise in a number of ways: by either an abnormal gene being switched on or by a normal gene being switched off; by chromosomal mutations or rearrangements which frequently result in abnormal or missing gene products in congenital conditions; or by the presence of an infectious agent in genetically normal individuals. In some cases, the total complement of mRNA, the products of gene expression, in an abnormal cell Will be different from that in a normal cell. In other cases, there may be no apparent difference in the level of gene expression, but the genetic lesion may be a subtle point mutation giving rise to a defective gene product.

Identification of differences in genetic expression or sequence between normal and abnormal cells is a powerful diagnostic and/or prognostic tool. It can also be the first step in understanding a disease by revealing its underlying mechanism. Thus, identification of genetic differences between normal and abnormal cells can provide a clear path to the design of new diagnostic tests, new drugs or gene therapy.

Methods for identifying and isolating sequences present or actively expressed in one cell but diminished or absent in another cell, referred to as "differential screening" and "difference cloning", have been applied to both genomic DNA and mRNA. Difference cloning is based upon subtractive hybridization, a method for isolating "target" sequences from one DNA population, referred to in this application as "tester", by using an excess of sequences from another DNA population, referred to in this application as "driver". One method of subtractive hybridization mixes a restriction endonuclease-digested tester DNA with an excess of randomly sheared driver DNA Lamar, et al., "Y-Encoded, Species-Specific DNA in Mice: Evidence That the Y Chromosome Exists in Two Polymorphic Forms in Inbred Strains", Cell, Vol. 37, pp. 171–177, (1984). The DNA mixture is denatured, hybridized and ligated into a compatible restriction site in a cloning vector. Only a tester DNA fragment reannealled to its complement would have both of the correct ends required for cloning. Conversely, any tester DNA fragments that anneal to complementary driver DNA fragments would not have both of the required ends. The low yield of cloned target sequences in this method is due primarily to the slow reannealling of dilute tester sequences to their complements. In addition, the enrichment of unique target sequences from a background of sequences common to the driver is limited by the initial excess of driver to tester.

Other methods of subtractive hybridization are directed toward the preparation of subtracted probes for differential screening of cDNA libraries by in situ colony blot hybridization. In differential screening, differentially expressed nucleic acids are not cloned, but are used as hybridization probes to identify and characterize unenriched cDNA clones. One method described by Kuze, et al., "A new vector and RNase H method for the subtractive hybridization", Nucleic Acids Research, Vol. 17, No. 2, pp. 807, (1989). prepares subtracted RNA probes using hybridization to DNA, followed by digestion with RNase H to separate non-hybridized RNA from the hybrid. After the remaining RNA is purified, the subtractive hybridization process is repeated. Hybridization of immobilized DNA using the purified subtracted RNA probe indicates that the subtracted probes can be enriched at least 100 fold. Kuze et al. does not describe a way in which the sequences of the subtracted RNA itself may be cloned or amplified, or suggest a use for the subtracted RNA other than as a hybridization probe.

Some improvements to the subtractive hybridization methods, as applied to difference cloning, involve the use of nucleic acid amplification processes selectively to increase the copy number of a DNA segment having the target sequence. An improvement to subtractive hybridization described by Wieland, et al., "A method for difference cloning: Gene amplification following subtractive hybridization", Proc. Natl., Acad. Sci. USA, Vol. 87, pp. 2720–2724, (1990). Uses the "polymerase chain reaction" (PCR) to increase the concentration of target sequences, and multiple steps of annealing tester DNA to excess driver DNA to further enrich the unique target sequences from a background of sequences common to the driver. in this procedure tester DNA fragments are first prepared for amplification by ligating to a "template" oligonucleotide. A mixture of prepared tester DNA and a 200-fold excess of randomly sheared driver DNA is denatured and reannealled to 90% completion, after which the remaining single-stranded DNA containing target sequences is purified from the double-stranded DNA containing the driver. After three rounds of denaturation, annealing and purification, the remaining tester DNA is then amplified in PCR using primers that anneal to the template sequences. The double-stranded PCR products are then cloned and sequenced. The method gave a 100- to 700-fold enrichment of target sequences.

Another improvement to subtractive hybridization described by Lisitsyn, et al., "Cloning the Differences Between Two Complex Gnomes", Science, pp. 946–951, (1993). is a technique called "representational difference analysis" (RDA). RDA lowers the complexity of both tester and driver genomic DNA by using various restriction endonucleases, eg. BamHI, Bg/II and HindIII, to generate fragments of a particular length that can be efficiently amplified in PCR as "representations" of the genome. The tester and driver fragments are ligated to dephosphorylated oligonucleotide adaptors such that an adaptor sequence is ligated to the 5'-end of each strand. The adapted fragments are then amplified in separate PCR reactions using the adaptor as a primer to achieve kinetic enrichment of a population of "amplicons" that are below 1 kb in size. Finally, the tester and driver amplicons is digested with the same restriction endonuclease to remove the original adaptors.

The "difference analysis" step of RDA is based upon the kinetic and subtractive enrichment of the tester amplicons in a second PCR. It begins with ligating different dephosphorylated oligonucleotide adaptors, this time only to the tester amplicons. An excess of driver amplicons are then mixed with the adapted tester fragments, denatured, and allowed to anneal. A portion of the annealed fragments is then treated with a DNA polymerase to allow extension of driver and adapted tester strands using the complementary driver or adapted tester strands as template. The annealed and extended amplicons are then amplified in PCR using the adaptor as a primer. Driver strands annealed to complementary driver strands will not be extended or amplified. Driver strands annealed to complementary adapted tester strands will be extended, but will lack a 5'-terminal adaptor sequence that is necessary to form a template for exponential amplification in PCR. Only the adapted tester strands that anneal to their complementary adapted tester strands and are extended prior to PCR will contain sequences on both 5' and 3' ends to enable exponential amplification.

Following 10 cycles of PCR, a portion of the amplified products is treated with a nuclease to specifically degrade single-stranded nucleic acids. After inactivating the nuclease, a portion of the remaining nucleic acid is further amplified in PCR using the same primer. After 15 to 20 more cycles of PCR, the double-stranded DNA products are digested with the restriction endonuclease, and the process of difference analysis is repeated. After sufficient rounds (typically 3 to 4, for example) of RDA are performed, the double-stranded DNA products are finally cloned and analyzed.

Although RDA was originally developed for genomic DNA, a variation of RDA has been more recently applied to cDNA Hubank, et al., "Identifying differences in mRNA expression by representational difference analysis of cDNA", Nucleic Acids Research, Vol. 22, No. 25, pp. 5640–5648, (1994). Since the cDNA population derived from a typical cell represents only 1–2% of the total genome, kinetic enrichment to reduce complexity should not be necessary for RDA when applied to cDNA. Dephosphorylated oligonucleotide adaptors are ligated to tester and driver cDNA fragments that are generated by digestion of the double-stranded cDNA with a frequently cutting restriction endonuclease, eg. DpnII. The adapted cDNA fragments are amplified separately by PCR and the resulting amplicons are digested with the same restriction endonuclease to remove the adaptor sequences. The tester cDNA amplicons are then subjected to multiple rounds of RDA as described for genomic DNA. Despite many successful applications of subtractive hybridization, the various methodologies have been described as "technically difficult, time consuming and often either impractical or unreliable" (Hubank and Schatz, 1994). One difficulty encountered with subtractive hybridization is the requirement for physical removal of hybridized tester sequences prior to amplification and/or cloning. Another limitation of subtractive hybridization is related to self-reassociation kinetics of complex genomes. Similarly, RDA shares some of the problems common to other subtractive hybridization methods. One is the requirement for self-reannealing of complementary tester sequences to enable amplification. For rare cDNA sequences (less than 1%, for example) this imposes kinetic limitations and requires lengthy hybridizations (of 20 hours, for example). Another limitation of RDA is the amplification of a double-stranded tester DNA that requires the use of an excess (typically 100-fold) of double-stranded driver DNA to compete with the re-annealing of complementary tester DNA strands. A single-stranded tester nucleic acid could more effectively hybridize with a complementary single-stranded driver DNA. To avoid physical removal of hybridized sequences, RDA requires the covalent activation and inactivation of tester sequences prior to amplification. [For subsequent rounds of RDA, these modifications must be removed with a restriction enzyme, new primers must be ligated and the newly modified tester must be subjected to hybridization with driver and activation/inactivation steps before the next application of PCR.] This multi-step process becomes a serious practical problem with RDA, in that the PCR amplification step is vulnerable to contamination by less enriched amplified products. Anti-contamination procedures cannot be implemented since the amplicons must remain intact and active as a template throughout the various steps of each round of RDA.

Thus, there is a need for a process for the enrichment of nucleic acid sequences which: 1) avoids hybrid removal prior to amplification; 2) does not require concentration-limiting self-annealing of tester nucleic acids; 3) utilizes single-stranded tester and driver nucleic acids; 4) avoids modification of the tester nucleic acids between rounds of subtractive hybridization and amplification; and 5) integrates hybridization, inactivation, and exponential amplification into a process with fewer steps, thus avoiding contamination.

SUMMARY OF THE INVENTION

The method of this invention, called subtractive amplification, represents a novel combination of subtractive hybridization and nucleic acid amplification. Subtractive amplification has the following advantages: 1) it avoids the physical removal of hybridized sequences before amplification; 2) it avoids a concentration-limiting self-annealing of tester nucleic acids in order to activate them for amplification; 3) it improves hybridization efficiency by using single-stranded tester and driver nucleic acids; 4) it avoids modification of the tester nucleic acids after the hybridization step to activate them for amplification; 5) it avoids modification of the tester nucleic acids between rounds of subtractive hybridization and amplification; 6) it allows a simple dilution procedure to prepare the products of one round of subtractive amplification reaction for the next round of subtractive amplification; and 7) it minimizes contamination by integrating multiple rounds of subtractive hybridization and exponential amplification into a process with fewer steps.

According to the method of the present invention, target RNA is preferentially amplified relative to non-target RNA in a sample of tester RNA. As used herein, tester RNA refers to RNA sequences which are to be subjected to subtractive amplification according to the present invention. Tester RNA includes both target and non-target RNA sequences, each containing terminal priming sequences to enable amplification. In the method, target RNA is preferentially amplified relative to any amplification of non-target RNA that may occur.

According to the method, a sample of tester RNA is contacted with driver sequences which are complementary to the non-target RNA under conditions where the driver sequences hybridize to the non-target RNA. A nucleic acid primer is then extended using the target RNA as a template, forming a DNA template complementary to some or all of the target RNA. The DNA template is then rendered single-stranded to enable the hybridization to it of a promoter template, and extended using the promoter template to form a DNA template comprising a functional double-stranded promoter. Multiple copies of the target RNA sequence can now be transcribed from the DNA template through recognition of the contained functional double-stranded promoter by RNA polymerase.

According to the method, the driver sequences, nucleic acid primer, and promoter template may be DNA or RNA, and are preferably DNA.

According to the method, the hybridization of driver sequences to the non-target RNA interferes with the ability of the non-target RNA to serve as a template. As a result, the nucleic acid primer is preferentially extended using the target RNA as a template for forming the DNA template, as opposed to using the non-target RNA as template. In one embodiment of the method, non-target RNA is inactivated as a template for DNA synthesis prior to the formation of the DNA template. Inactivation of the non-target RNA may be performed by a variety of methods including, for example, digesting any non-target RNA which is hybridized to a driver sequence. Digestion of non-target RNA may be performed, for example, by any enzyme having ribonucleolytic activity analogous to that of ribonuclease H enzyme.

After its formation, the DNA template is preferably rendered single-stranded. This may be accomplished by digesting any target RNA hybridized to the DNA template, for example, using any enzyme having ribonucleolytic activity analogous to that of ribonuclease H enzyme. The DNA template may also be rendered single-stranded through strand separation, for example, by heat denaturation.

The promoter template includes a sequence capable of forming a functional promoter. In one embodiment, the promoter template comprises sequences capable of forming a functional promoter and a transcription initiation site from a bacteriophage. In a preferred embodiment, the bacteriophage is T7.

According to the present invention, the DNA template and/or the extended DNA template can be amplified prior to target RNA synthesis. This amplification can be performed by a variety of nucleic acid amplification methods known in the art and is preferably performed either by the PCR (polymerase chain reaction) or SDA (strand displacement amplification) or NASBA (nucleic acid sequence-based amplification) methodologies.

In one embodiment of the present invention, the synthetic target RNA is synthesized from the extended DNA complement, the single-stranded DNA template containing a functional double-stranded promoter, by transcription utilizing RNA polymerase. In a further embodiment, the synthetic target RNA so transcribed may be further amplified by a RNA amplification reaction, preferably by NASBA.

Subtractive amplification can be performed in multiple cycles where the sample of tester RNA being used in the subtractive amplification process is synthetic target RNA obtained from a prior subtractive amplification. Driver sequences for a subsequent cycle of subtractive amplification can also be obtained from a prior subtractive amplification.

In one particular embodiment, subtractive amplification is performed by:
a) contacting the sample of tester RNA with driver sequences which are complementary to the non-target RNA under conditions where the driver sequences hybridize to the non-target RNA;
b) contacting the target RNA with nucleic acid primers under conditions suitable for hybridization;
c) extending those nucleic acid primers which hybridize to the target RNA to form a DNA template complementary to some or all of the target RNA;
d) making the DNA template single-stranded;
e) contacting, under hybridizing conditions, the single-stranded DNA template with a nucleic acid sequence capable of acting as a promoter template;
f) extending those DNA templates which hybridize to the promoter template to form extended DNA templates comprising both a functional double-stranded promoter portion and a single-stranded portion capable of acting as a template; and
g) transcribing the extended DNA template to form multiple copies of synthetic target RNA.

According to a preferred embodiment of the method, target RNA present in a sample of tester RNA is preferentially amplified relative to non-target RNA present in the tester, both target and non-target RNA containing terminal priming sequences to enable amplification, by performing the following reactions: (1) a hybridization reaction, wherein the sample of tester RNA-contacts driver sequences under conditions such that the driver sequences which are complementary to the non-target RNA hybridize, and prevent the hybridized non-target RNA from functioning as templates for nucleic acid synthesis; (2) a reverse transcription reaction, wherein nucleic acid primers hybridize to the target RNA from the hybridization reaction and are extended using a reverse transcriptase, thereby forming a DNA template; (3) a DNA conversion reaction, wherein DNA templates from the reverse transcription reaction are made single-stranded, hybridized to a promoter template, and extended using the DNA polymerase, thereby forming DNA templates with a functional double stranded promoter; and (4) a transcription reaction, wherein DNA templates with functional double stranded promoters from the DNA conversion reaction are transcribed using an RNA polymerase, thereby forming from each DNA template one or more copies of the target RNA.

According to one aspect of the preferred embodiment, in each step of the process all or a portion of one reaction may be added to a subsequent reaction. In another aspect of the preferred embodiment, the hybridization reaction is performed by adding the tester RNA to a medium comprising driver sequences under conditions such that the driver sequences hybridize with non-target RNA. In another aspect of the preferred embodiment, the reverse transcription reaction is performed by adding a portion of the hybridization reaction to a medium comprising a first primer and a reverse transcriptase under conditions such that DNA templates are formed. In another aspect of the preferred embodiment, the DNA conversion reaction is performed by adding a portion of the reverse transcription reaction to a medium comprising a DNA polymerase and a promoter template under conditions such that DNA templates with functional double-stranded promoters are produced. In another aspect of the preferred embodiment, the transcription reaction is performed by adding a portion of the DNA conversion reaction to a medium comprising an RNA polymerase under conditions such that target RNA is produced.

According to one embodiment of the process, the driver nucleic acid sequences are composed of DNA. In one aspect of this embodiment, a portion of the hybridization reaction is added to a degradation reaction medium comprising a ribonuclease that hydrolyzes the RNA of an RNA:DNA hybrid under conditions such that the RNA tester sequences that anneal to the DNA driver sequences (non-target RNA) are degraded, and a portion of the degradation reaction is added to the reverse transcriptase reaction, hence providing target RNA sequences. In another aspect of this embodiment, the hybridization reaction medium further comprises a ribonuclease that hydrolyzes the RNA of an RNA:DNA hybrid under conditions such that the RNA tester sequences that anneal to the DNA driver sequences (non-target RNA) are degraded. Another aspect of this embodiment relates to the particular ribonucleases that may be used.

According to another embodiment of the process, a portion of the reverse transcription reaction is added to a degradation reaction medium comprising a ribonuclease that hydrolyzes the RNA of an RNA:DNA hybrid under conditions such that the RNA tester sequences forming a hybrid with the DNA templates are degraded, and a portion of the degradation reaction is added to the DNA conversion reaction, hence providing DNA templates.

According to another embodiment of the process, a portion of the reverse transcription reaction is added to a denaturation reaction under conditions such that the DNA templates are separated from the RNA tester sequences of the RNA:DNA hybrid, and a portion of the denaturation reaction is added to the DNA conversion reaction, hence providing DNA templates.

According to another embodiment of the process, the reverse transcription reaction medium further comprises a ribonuclease that hydrolyzes the RNA of an RNA:DNA hybrid under conditions such that the RNA tester sequences forming a hybrid with the DNA template are degraded.

According to another embodiment of the process, a portion of the reverse transcription reaction is added to a DNA amplification reaction medium comprising the first primer, a second primer and a DNA polymerase under conditions such that the DNA template hybridizes to the second primer and is extended using the DNA polymerase to form a double-stranded DNA and the strands of the double-stranded DNA are separated, upon which a cycle ensues wherein: i) the first primer and the second primer each hybridize to their complementary DNA strands; ii) each primer is then extended using the DNA polymerase to form a double-stranded DNA; and iii) the complementary DNA strands of the double-stranded DNA are separated, and thereafter a portion of the DNA amplification reaction is added to the DNA conversion reaction, hence providing DNA templates.

In one aspect of this embodiment, the DNA amplification reaction is the polymerase chain reaction, wherein the complementary DNA strands of the double-stranded DNA are separated by adjusting the reaction conditions to cause denaturation. In another aspect of this embodiment, the DNA amplification reaction is by strand displacement amplification, wherein the reaction medium further comprises a restriction endonuclease under conditions that the restriction endonuclease nicks the primers of the double-stranded DNA and the complementary DNA strands of the double-stranded DNA are separated by the DNA polymerase extending the nicked primers to displace the complementary DNA strands.

According to another embodiment of the process, the DNA conversion reaction medium further comprises a first primer, and the promoter template therein further comprises a second primer under conditions such that the DNA template hybridizes to the second primer and is extended using the DNA polymerase to form a double-stranded DNA, upon which a cycle ensues wherein: i) the complementary DNA strands of the double-stranded DNA are separated; ii) the first primer and the second primer each hybridize to their complementary DNA strands; and iii) each primer is then extended using the DNA polymerase to form a double-stranded DNA, thereby forming DNA templates with functional double-stranded promoters.

In one aspect of this embodiment, the complementary DNA strands of the double-stranded DNA are separated by adjusting the reaction conditions to cause denaturation. In another aspect of this embodiment, the reaction medium further comprises a restriction endonuclease under conditions that the restriction endonuclease nicks the primers of the double-stranded DNA and the complementary DNA strands of the double-stranded DNA are separated by the DNA polymerase extending the nicked primers to displace the complementary DNA strands.

According to another embodiment of the process, the reverse transcription, DNA conversion and transcription reactions together comprise an RNA amplification reaction, wherein tester RNA sequences are provided in a medium comprising a first primer, a promoter template, a reverse transcriptase, a DNA polymerase and an RNA polymerase under conditions such that the tester RNA sequences hybridize to the first primer and provide templates for synthesis of DNA templates by extension of the annealed first primer using the reverse transcriptase, thereby forming RNA:DNA hybrids, the RNA strands of which are degraded; the DNA templates hybridize to the promoter template and are extended using the DNA polymerase, thereby forming DNA templates each with a functional double-stranded promoter; and the RNA polymerase recognizes each double-stranded promoter and synthesizes from the DNA templates copies of the target RNA sequences.

In one aspect of this embodiment, the DNA polymerase is reverse transcriptase. In another aspect of this embodiment, the RNA amplification reaction medium further comprises a ribonuclease that hydrolyzes the RNA of an RNA:DNA hybrid under conditions such that the RNA tester sequences forming hybrids with the DNA templates are degraded. In another aspect of this embodiment, a portion of the hybridization reaction comprising the tester RNA sequences that do not anneal to the driver sequences is added to the RNA amplification reaction, hence providing tester RNA sequences. In another aspect of this embodiment, target RNA sequences from one round of the RNA amplification reaction provide tester RNA sequences in a subsequent round of the RNA amplification reaction. In another aspect of this embodiment, a portion of the RNA amplification reaction comprising target RNA sequences from one round of the process is added to the hybridization reaction of a subsequent round of the process, hence providing tester RNA sequences.

According to another embodiment of the process, target RNA sequences from one round of the process provide tester RNA sequences in a subsequent round of the process. In one aspect of this embodiment, a portion of the transcription reaction comprising target RNA sequences from one round of the process is added to the hybridization reaction of a subsequent round of the process, hence providing tester RNA sequences.

According to another embodiment of the process, a mixture of RNA comprising target RNA sequences and each comprising terminal priming sequences are added to the hybridization reaction, hence providing tester RNA sequences.

According to another embodiment of the process, the hybridization reaction further comprises an RNA polymerase, and to which is added a mixture of DNA templates each with a functional double-stranded promoter, under conditions such that the RNA polymerase recognizes each double-stranded promoter and synthesizes from the DNA templates copies of a mixture of RNA comprising target RNA sequences and each comprising terminal priming sequences, hence providing tester RNA sequences. In one aspect of this embodiment, terminal sequences and a double-stranded promoter are appended to DNA templates from which tester RNA sequences are synthesized using an RNA polymerase.

According to another embodiment, a final round of the subtractive amplification process comprises: 1) a hybridization reaction; 2) a reverse transcription reaction; 3) a DNA duplexing reaction, wherein DNA templates from the reverse transcription reaction are provided in a medium comprising a DNA polymerase and a second primer under conditions such that the DNA templates hybridize to the second primer and provide templates for synthesis of double-stranded DNA templates by extension of the annealed second primer using the DNA polymerase.

According to one aspect of this embodiment, the DNA duplexing reaction is performed within a DNA amplification reaction wherein the DNA duplexing reaction medium further comprises a first primer under conditions such that the second primer hybridizes to the DNA templates and is extended using the DNA polymerase to form double-stranded DNA templates, upon which a cycle ensues wherein: i) the complementary DNA strands of each double-stranded DNA template is separated; ii) the first primer and the second primer each hybridizes to their complementary DNA template strands; and iii) each primer is then extended using the DNA polymerase to form double-stranded DNA templates.

According to another aspect of this embodiment, the double-stranded DNA templates of the duplexing reaction are characterized by cloning and sequencing. In one aspect of this embodiment, the characterized sequences are used to make hybridization probes or amplification primers. In another aspect of this embodiment, the characterized sequences are used to identify or characterize a useful nucleic acid sequence. In another aspect of this embodiment, the cloned DNA templates are used for the preparation of tester RNA sequences or driver nucleic acid sequences.

The present invention also relates to kits for performing subtractive amplification according to the present invention. In general, these kits may include any compilation of RNA and DNA sequences and enzymes used to perform subtractive amplification according to the method of the present invention. In one embodiment, the kit includes a nucleic acid primer capable of hybridizing to a target RNA under conditions suitable for extension of the nucleic acid primer, and a promoter template capable of hybridizing to a DNA complement of the target RNA under conditions suitable for extension of the DNA complement such that a functional promoter is formed which is capable of transcribing the DNA complement such that multiple copies of target RNA are synthesized. In this kit, the nucleic acid primer and promoter template are preferably DNA. The promoter template may include sequences capable of forming a promoter and transcription initiation site from a bacteriophage. One type of bacteriophage may be T7. The kit may also include one or more enzymes which are used to perform one or more of the steps of subtractive amplification according to the present invention. Examples of these enzymes include: reverse transcriptase; a ribonuclease capable of digesting non-target RNA hybridized to a driver sequence, such as an enzyme having the ribonucleolytic activity of ribonuclease H; a RNA polymerase; and a DNA polymerase.

DETAILED DESCRIPTION OF THE PREFERRED EMBODIMENTS

Figure 1:
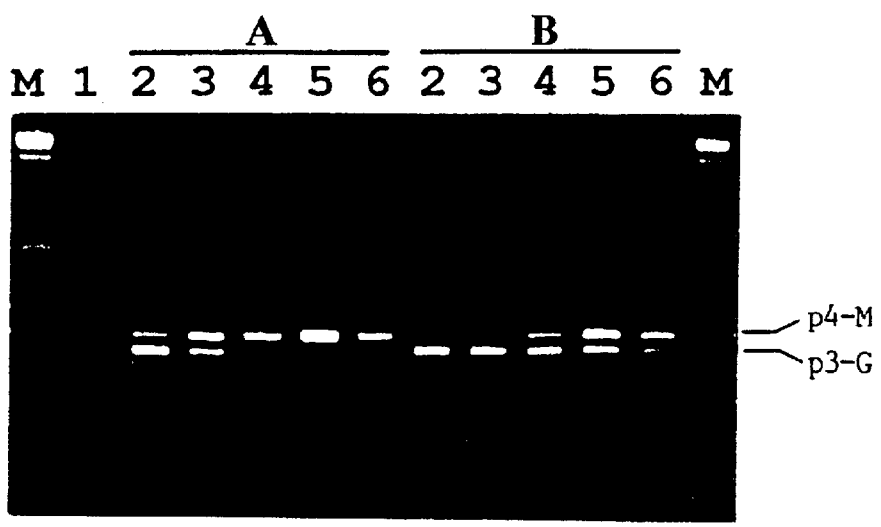
FIG. 1 shows agarose gel electrophoretic analysis of the products of subtractive amplification using PCR, where (I) is a photograph of the products detected by ethidium bromide staining, and (II) is an autoradiogram of the products detected by blot hybridization to radiolabeled oligonucleotide probes.
Figure 1:
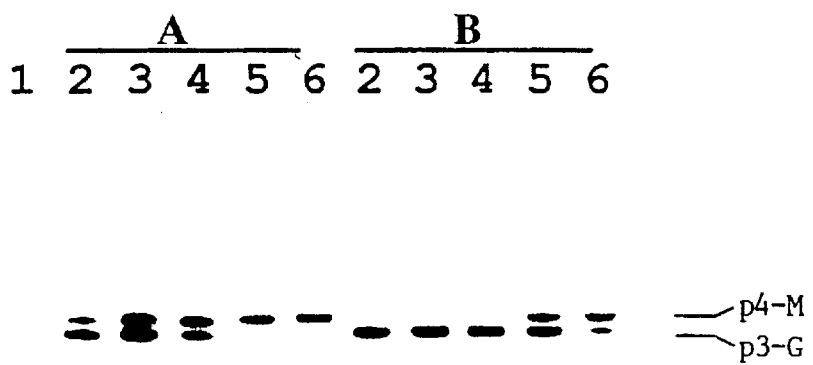

This invention relates to a process for the preferential amplification of target RNA sequences present in a mixture of tester RNA sequences that are either absent or less represented in a mixture of driver nucleic acid sequences. The tester RNA and driver nucleic acid sequences are prepared from nucleic acids isolated from at least two different populations of cells. The tester RNA and driver nucleic acid sequences are of opposite senses; for example, the tester RNA may have the same sense as the mRNA of a cell (+sense), while the driver nucleic acid would have the sense complementary to that of the mRNA (−sense). The target RNA sequences are a subset of the tester RNA sequences. Those sequences that would be complementary to the target RNA sequences are either absent or less represented among the population of driver nucleic acid sequences. Target RNA sequences can be operationally defined as those of the tester RNA sequences that do not anneal to the driver nucleic acid sequences.

This process can be applied to the discovery of target RNA sequences encoding proteins, such as cytokines, hormones, growth factors or receptors, by using tester RNA sequences prepared from induced cells and driver nucleic acid sequences prepared from uninduced control cells. A kit for this process comprising a number of receptacles containing the reagents required for the process may be contemplated. The application of this process results in useful products. For example, the enriched target nucleic acid sequences when amplified by the process of this invention or the proteins encoded by these target nucleic acid sequences. The process can be used to find target RNA sequences representing infectious agents, for example viruses or bacteria, by using tester RNA sequences prepared from infected samples and driver nucleic acid sequences from uninfected controls. The process can also be used to isolate target nucleic acid sequences responsible for a disease, disorder, or abnormal physical state, for example to find causes for human health problems, e.g. inherited disorders, or cancer, by using nucleic acids from diseased test cells and normal control cells. The use of the process of this invention to diagnose may also be contemplated. The unique nucleic acid sequences identified by this process could be used for diagnostic purposes or for gene therapy or as targets for the discovery of pharmaceuticals. The proteins that are encoded by the sequences could be used for preparing appropriate immunodiagnostic reagents. The encoded proteins could also be used therapeutically either on their own as biopharmaceuticals or as targets for the discovery of pharmaceuticals.

For a general application where the target RNA sequences represent uniquely or more abundantly expressed gene sequences, the tester RNA sequences and driver nucleic acid sequences are both derived from the mRNA of their respective cell populations. In order to utilize the mRNA for the preparation of tester RNA sequences and driver nucleic acid sequences, a complementary DNA or cDNA is generally prepared from each mRNA. Various methods for the preparation and cloning of cDNA from natural RNA are known in the art. Thereby methods for preparing cDNA from natural RNA are not limited to those described hereinafter.

First, an RNA-specific primer may be hybridized to the natural RNA and extended to synthesize a cDNA using reverse transcriptase, thereby forming an RNA-DNA hybrid. The RNA-specific primer typically comprises a 3' terminal oligo(dT) sequence that hybridizes to a 3'-terminal polyadenylated sequence that is present in most eukaryotic mRNAs. The RNA-specific primer may further comprise a mixture of sequences of the general formula oligo(dT)VN 3', to avoid synthesis of cDNA from the polyadenylated sequence. Alternatively, a different type of RNA-specific primer may be used for synthesis of cDNA from RNA without using a 3'-terminal polyadenylated sequence. This later type of RNA-specific primer may comprise a mixture of short 3'-terminal oligonucleotide sequences of random composition, or a single arbitrary sequence that hybridizes to the RNA under conditions of low stringency. The RNA-specific sequence may further comprise a recognition site for a restriction endonuclease to enable directional cloning of the cDNA in a plasmid or phage vector.

Second, a cDNA-specific primer may be hybridized to the cDNA and extended to synthesize a double-stranded cDNA using a DNA polymerase. Some methods of second strand cDNA synthesis call for the removal of the RNA strand that is hybridized to the cDNA before hybridization of the cDNA-specific primer. This can be accomplished by thermal or chemical denaturation or by chemical or enzymatic hydrolysis of the RNA strand.

The cDNA-specific primer may comprise a mixture of short 3'-terminal oligonucleotide sequences of random composition, or a single arbitrary sequence that hybridizes to the cDNA under conditions of low stringency. Alternatively, the 3' terminus of the cDNA may anneal to another sequence of the same cDNA to form a self-priming hairpin loop. Other methods of second strand cDNA synthesis do not require the removal of the RNA strand, but rather partially hydrolyze the RNA strand with RNase H to provide oligoribonucleotide primers hybridized to the cDNA that are extended using a DNA polymerase to form a double-stranded cDNA.

Finally, the double-stranded cDNA may be subjected to a replication process. Some methods involve the ligation of the double-stranded cDNA into a plasmid or phage vector to allow for the generation of libraries and the cloning of individual sequences. Before ligation into cloning vectors, the double-stranded cDNA is generally first prepared by ligating to oligonucleotide linkers or adapters to each of its ends. Other methods of cDNA replication involve nucleic acid amplification processes, such as PCR, in which the double-stranded cDNA is added to a reaction comprising the RNA-specific primer and the cDNA-specific primer.

Although tester RNA sequences and driver nucleic acid sequences are derived from different populations of cells, it is preferable to use the same method to prepare cDNA from the RNA from each cell population. The cDNA synthesized from each cell population is then specifically adapted for generating either tester RNA sequences or driver nucleic acid sequences.

Each of the tester RNA sequences comprise terminal priming sequences that enable the hybridization of primers for purposes of DNA polymerization, hence amplification. The first primer hybridizes to the tester RNA sequences at their 3'-terminal priming sequences and is extended with a DNA polymerase (reverse transcriptase) to form DNA templates. The DNA templates hybridize at their 3' terminal priming sequences to the promoter template and are extended with a DNA polymerase to form a double-stranded promoter attached to each DNA template. Additionally, if the promoter template further comprises the second primer, then the DNA polymerase further extends the second primer to form a double-stranded DNA comprising the DNA template and a double-stranded promoter. The priming sequences are of sufficient length and base composition to enable hybridization with their respective primers under the conditions suitable for the DNA polymerases.

The tester RNA sequences can be prepared by a variety of methods, not limited to those described hereinafter. Tester RNA sequences can be preferably generated by in vitro transcription of DNA templates that are each joined to a double-stranded promoter and are complementary to tester RNA sequences such that an RNA polymerase recognizes the double-stranded promoter and synthesizes copies of the tester RNA sequences from the DNA templates. Prior to such in vitro transcription, the priming sequences may be added to the DNA templates by ligation of primers, annealed with their complementary adapters, to the ends of the DNA templates that are generated using restriction endonucleases Lisitsyn, et al., "Cloning the Differences Between Two Complex Gnomes", Science, pp. 946–951, (1993). The restriction endonucleases preferably generate a 5'-terminal single-stranded sequence of typically four nucleotides in length. The 5'-terminal sequence used to ligate the first primer and its adapter is preferably different from the 5'-terminal sequence used to ligate the second primer and its adapter. For example, the restriction endonuclease Sau3AI may be used to generate 5'-terminal single-stranded GATC sequences to which is ligated the first primer annealed to its adapter, whereas the restriction endonuclease MluI may be used to generate 5'-terminal single-stranded CGCG sequences to which is ligated the promoter template comprising the second primer annealed to its adapter. The DNA templates from which the tester RNA sequences are generated may be obtained from either a mixture of cDNA synthesized directly from mRNA by reverse transcription or a library of cDNA cloned in a plasmid or phage vector.

The driver nucleic acid sequences may be composed of any nucleic acid that when hybridized to the tester RNA sequence will impair the capability of the tester RNA sequences to serve as a template for a DNA polymerase, that is a reverse transcriptase. The driver nucleic acid may block the RNA template from a DNA polymerase that is incapable of displacing it during extension of the first primer. Alternatively, the hybridization of driver nucleic-acid to the tester RNA may provide a substrate for enzymatic RNA hydrolysis. As such, any method for preparing the driver nucleic acid sequences should provide a strand of nucleic acid that would be complementary to the tester RNA sequences.

In the preferred embodiment of the process, the driver nucleic acid sequences are composed of DNA. The driver DNA sequences are single-stranded in the hybridization reaction, but may originate from a double-stranded DNA or RNA-DNA hybrid. Methods for the preparation of single-stranded driver DNA must ensure that the sense that is complementary to the tester RNA is provided in the hybridization reaction. A single-stranded DNA may be obtained from a double-stranded DNA by thermal denaturation or by selective degradation of one strand by a 3' or 5' exonuclease, for example. A single-stranded driver DNA may be obtained from phage particles that package a single-stranded genomic DNA, M13 for example, or from phage particles that contain a single-stranded plasmid, a phagemid for example, with phage replication and packaging sequences, an f1 origin of replication, for example. Alternatively, the single-stranded driver DNA may be obtained from a cDNA synthesized from an mRNA.

Certain embodiments of this invention involve the use of nucleic acid amplification methods to increase the copy number of target sequences. Amplification methods can be used for either diagnostic or discovery applications. For diagnostic purposes, primers are designed for specificity to a particular nucleic acid sequence that may be present in the sample. The nucleic acid sequence is generally already known to the user. For discovery purposes, the nucleic acid sequence is unknown. Application of the amplification process requires adaptations of the nucleic acids to provide particular sequences that are specific to the primers. Many nucleic acid amplification processes known in the art are signal amplification methods, which merely alter the oligonucleotide sequences that are initially present in the reaction in response to the added target sequence. Hence, signal amplification processes are not suitable for discovery of new sequences. There are only three known amplification processes that actually generate target-specific sequence information that is not initially present in the reaction, and are useful for sequence discovery.

U.S. Pat. No. 4,683,202 to Mullis describes an amplification process, known as the "polymerase chain reaction" (PCR), which involves the use of two primers and a DNA polymerase. In general, PCR involves treating the sample suspected of containing a target DNA sequence with oligonucleotide primers such that a primer extension product is synthesized by a DNA polymerase. The primer extension product DNA strand is separated from the template strand in the preferred embodiment using heat denaturation. Both the original template and the primer extension product then serve as templates in the next and subsequent cycles of extension, resulting approximately in the doubling of the number of target DNA sequences in the sample at the end of each cycle. Consequently, multiple cycles result in the quasi-exponential amplification of the target nucleic acid sequence. Optimal practice of the PCR requires the use of a thermocycler capable of rapid changes of temperature and of a DNA polymerase, such as Taq polymerase (U.S. Pat. No. 4,683,195) that resists the denaturation caused by repeated exposure to temperatures above 90° C. required to separate the DNA strands.

U.S. Pat. No. 5,455,166 to Walker of Becton Dickinson Co. describes another nucleic acid amplification process, referred to as "strand displacement amplification" (SDA), with exponential reaction kinetics that takes place at a relatively constant temperature throughout and without serial addition of reagents. An SDA reaction contains two enzymes, a restriction endonuclease and a DNA polymerase, two primers, each of which have a central restriction site, and an α-thioated deoxynucleoside triphoshate. Its 8-step cyclic process repeats the following steps for each strand of the DNA product: (1) the first primer anneals to a first single-stranded DNA product; (2) the DNA polymerase uses the first primer and first single-stranded DNA product for bidirectional synthesis of an a-thioated double-stranded DNA product; (3) the restriction endonuclease nicks the primer of the a-thioated double-stranded DNA product; and (4) the DNA polymerase extends the nicked primer to synthesize a new strand of the double-stranded DNA product while simultaneously displacing a second single-stranded DNA product. The second single-stranded DNA product, which is complementary to the first single-stranded DNA product, then anneals with the second primer and is used to make the original first single-stranded DNA product by repeating the first four steps to complete the cycle.

U.S. Pat. No. 5,409,818 to Davey et al. of Cangene Corporation describes an amplification process which involves the use of a first primer, a second primer which has a promoter, an RNA polymerase, a DNA polymerase (a reverse transcriptase) and a ribonuclease (RNase H) that specifically degrades the RNA strand of an RNA-DNA hybrid. The cyclic process takes place at a relatively constant temperature throughout and without serial addition of reagents, wherein the first primer hybridizes to the RNA product, reverse transcriptase uses the RNA product as template to synthesize a DNA product by extension of the first primer, RNase H degrades the RNA of the resulting RNA-DNA hybrid, the second primer with the promoter hybridizes to the DNA product, reverse transcriptase uses the second primer as template to synthesize a double-stranded promoter by extension of the DNA product, and RNA polymerase uses the promoter and DNA product to transcribe multiple copies of the same RNA product. In the most commonly practiced embodiment of this invention, in a process referred to as NASBA, the ribonuclease from the reverse transcriptase is supplemented with a cellular RNase H. U.S. Pat. No. 5,130,238 to Malek et al. of Cangene Corporation describes an enhanced nucleic acid amplification process that is similar to that described in U.S. Pat. No.

5,409,818, but is enhanced by addition to the reaction mixture of an alkylated sulfoxide (for example, dimethyl sulfoxide) and BSA.

The process of the present invention, subtractive amplification, can be described as a four-step process. It will be understood that the numbering of steps in the process is of purely heuristic value in defining the relative order of molecular events but not the actual number of reactions that may be performed. The reactions of two or more steps may be combined into a single reaction medium and performed as one step. Also additional reactions may be interpolated between steps. Similarly, each reaction is performed in a medium, as designated, and under conditions that enable the reaction. More than one reaction may be performed in the same medium under the same or different conditions.

The first step of the process comprises a hybridization reaction wherein the tester RNA sequences are provided in a medium comprising driver nucleic acid sequences under conditions such that driver sequences hybridize with complementary tester sequences, the tester sequences that hybridize to driver sequences (referred to herein as "non-target RNA") being thereby rendered incapable of functioning as templates for nucleic acid synthesis. In the preferred embodiment, a mixture of RNA comprising target RNA sequences, with each RNA comprising terminal priming sequences, is added to the hybridization reaction, hence providing tester RNA sequences.

The hybridization reaction is performed under appropriate conditions of pH, ionic strength and temperature to ensure that the driver hybridizes effectively and specifically to complementary sequences in the mixture of tester RNA sequences. Hybridization conditions may be selected among those that are described in the art, not limited to the following references cited herein: Sambrook, et al., "Dot and Slot Hybridization of RNA", Molecular Cloning: A Laboratory, pp. 7.53–7.55, (1989). Lisitsyn, et al., "Cloning the Differences Between Two Complex Gnomes", Science, pp. 946–951, (1993).; Hubank and Schatz, 1994; and Rosen, et al., "Subtractive Hybridization: A Technique for Isolation of Differentially Expressed Genes", Toxicology Methods, Vol. 4, No. 2, pp. 135–147, (1994). In addition, certain agents or solvents may be included in the hybridization reaction that increase specificity, facilitate hybridization at a lower temperature, or increase the hybridization kinetics. It is preferable that the hybridization conditions are compatible with any enzymes that are used subsequently to or concomitantly with the hybridization reaction. It is contemplated that the hybridization products may be purified from any incompatible components of the hybridization reaction before subsequent steps of the process.

The hybridization reaction may further comprise such agents that may promote the degradation or inactivation of the non-target RNA. This degradation or inactivation would supplement the inhibition by hybridized driver nucleic acid sequences of strand displacement during extension of the first primer with the reverse transcriptase. In the preferred embodiment, the hybridization reaction medium further comprises a ribonuclease, an RNase H, that hydrolyzes the RNA of an RNA:DNA hybrid under conditions such that the non-target RNA is degraded. The RNase H which could be used in this embodiment may be any enzyme capable of hydrolyzing any RNA that is annealed to any complementary DNA, and not capable of hydrolyzing single or double-stranded RNA or any DNA. Preparations comprising the RNase H should be relatively free of contaminating agents with DNase or RNase activities. Additionally, the RNase H that is used in this embodiment should be preferably capable of remaining stable and active under the hybridization conditions so that the non-target RNA may be hydrolyzed during the hybridization reaction. Preparations of such ribonucleases that are stable at elevated temperatures and uses thereof are taught in U.S. Pat. No. 5,459,055 to Jendrisak, et al of Epicentre Technologies Corporation. A thermostable bacterial RNase H that is suitable for this purpose may be selected from *Thermus thermophilus, Thermus flavus* or any other thermophilic bacteria known in the art.

Alternatively, in another embodiment, a portion of the hybridization reaction may be added to a degradation reaction medium comprising a ribonuclease, an RNase H, that hydrolyzes the RNA of an RNA:DNA hybrid under conditions such that non-target RNA that hybridizes to the driver DNA sequences is degraded. The RNase H which could be used in this embodiment should have the same activities and qualities as set forth in the aforementioned embodiment, with the single exception of remaining stable and active under the hybridization conditions. Since the hydrolysis of the non-target RNA may be performed at conditions other than those used for hydridization, the RNase H that is suitable for this purpose may be selected from *Escherischia coli* or any other bacteria known in the art.

The second step of the process comprises a reverse transcription reaction, wherein tester sequences from the hybridization reaction are provided in a medium comprising a first primer and a reverse transcriptase under conditions such that the tester RNA sequences that do not anneal to the driver nucleic acid sequences hybridize to the first primer (i.e., target RNA) and provide templates for synthesis of DNA templates by extension of the annealed first primer using the reverse transcriptase, thereby forming RNA:DNA hybrids, the RNA strands of which are degraded. In the preferred embodiment of the process, the RNA tester sequences are provided by adding a portion of the hybridization or degradation reactions to the reverse transcription reaction. In one embodiment of this process the reverse transcription reaction comprises part of an RNA amplification method, for example, NASBA.

The first primer is an oligodeoxyribonucleotide comprising a 3'-terminal sequence which is complementary to the 3'-terminal priming sequence of the tester RNA sequences. The first primer is of a particular length and base composition to allow specific and efficient synthesis of DNA templates from the tester RNA sequences under the conditions of the reverse transcription reaction. The first primer should also have a 3'-terminal sequence that minimizes annealing to itself or another primer in the reaction such that a primer would be extended using itself or another primer as template in a DNA or RNA amplification reaction, hence producing what is described in the art as "primer-dimers". It is contemplated that the first primer may be composed in part of nucleotides other than deoxyribonucleotides provided that a first primer of such composition may still function as template for DNA and RNA synthesis.

The reverse transcriptase which is used in this invention may be any enzyme capable of synthesizing DNA from an oligonucleotide primer and an RNA template. In addition to RNA-directed DNA polymerase, this enzyme may further comprise activities for DNA-directed DNA polymerase and RNase H. Preparations comprising the reverse transcriptase should be relatively free of contaminating agents with DNase or RNase activities. Additionally, the reverse transcriptase should be capable of remaining stable and active under the reverse transcription reaction conditions. In the preferred embodiment, a retroviral DNA polymerase is used. For example, in subtractive amplification using PCR, the reverse transcriptase from Maloney murine leukemia virus (MMLV) is used. Subtractive amplification with NASBA uses the reverse transcriptase from avian myeloblastosis virus (AMV) in the RNA amplification reaction. Certain DNA-directed DNA polymerases known in the art having RNA-directed DNA polymerase activity under certain reaction conditions may also be used in this invention. For example, a method is described for performing RT-PCR using the thermostable DNA polymerase from *Thermus thermophilus* in the presence of manganese (II) salts to relax the natural specificity for DNA templates and allowing DNA synthesis also from RNA templates Myers, et al., "Reverse Transcription an dDNA Amplification by a Thermus thermophilus DNA Polymerase", Biochemistry, Vol. 30:31, pp. 7661–7666, (1991). If the reverse transcriptase reaction is to be followed immediately by PCR, then degradation of the tester RNA template is unnecessary. It is further contemplated that other enzymes and conditions that are used to commence PCR from an RNA template may be employed in the reverse transcriptase reaction of this process.

The reverse transcription reaction comprises the necessary concentrations of cofactors and nucleoside triphosphates for DNA synthesis using the particular reverse transcriptase. The reverse transcription reaction is performed under the conditions of pH, ionic strength and temperature that are appropriate to the enzyme which is used. Such reaction conditions are known to those skilled in the art.

The third step of the process comprises a DNA conversion reaction, wherein DNA templates from the reverse transcription reaction are provided in a medium comprising a DNA polymerase and a promoter template under conditions such that the DNA templates hybridize to the promoter template and are extended using the DNA polymerase, thereby forming DNA templates with functional double-stranded promoters. In the preferred embodiment, the DNA templates are provided by adding a portion of the reverse transcriptase reaction to the DNA conversion reaction.

The promoter template is an oligodeoxyribonucleotide comprising a 3'-terminal sequence which is complementary to the 3'-terminal priming sequence of the DNA templates. The promoter template is of a particular length and base composition to allow specific and efficient synthesis of double-stranded promoters by extension of the DNA templates under the conditions of the DNA conversion reaction. The promoter template contains the plus (+) sense sequence of a promoter and transcription initiation site. This sequence, when used as a template in the DNA conversion reaction, contains sufficient information to allow specific and efficient binding of a RNA polymerase and initiation of transcription at the desired site. In the preferred embodiment, the promoter and initiation sequence are specific for the RNA polymerase from the bacteriophage T7. The plus (+) sense sequence of the T7 RNA polymerase promoter typically comprises the 17-nucleotide sequence 5'-TAATACGACTCACTATA-3' (SEQ. ID. NO. 1), which is immediately followed by a purine-rich initiation site sequence, typically 5'-GGGAGA-3'. In addition, the promoter template contains a short 5'-terminal sequence of preferably five nucleotides that precedes the promoter, which has been shown in the art to increase the efficiency of transcription Fahy, et al., "Self-sustained sequence replication (3SR):An Isothermal Transcription-based Amplification System Alternative to PCR", PCR Methods and Applications, pp. 25–33, (1991). In the preferred embodiment, the 5-terminal sequence of the promoter template is 5'-AATTCTAATACGACTCACTATAGGGAGA-3' (SEQ. ID. NO. 2). It is understood by those skilled in the art that some changes may be made in the promoter and initiation sequences specified herein and still achieve sufficient levels of transcription.

In some embodiments, the promoter template further comprises a second primer of a particular length and base composition to allow specific and efficient synthesis of a double-stranded DNA by extension of the second primer. The second primer should also have a 3'-terminal sequence that minimizes annealing to itself or another primer in the reaction such that a primer would be extended using itself or another primer as template in a DNA or RNA amplification reaction, hence producing what is described in the art as "primer-dimers". It is contemplated that the second primer may be composed in part of nucleotides other than deoxyribonucleotides provided that a first primer of such composition may still function as template for DNA and RNA synthesis.

The DNA polymerase which is used in this invention may be any enzyme capable of synthesizing DNA from an oligodeoxyribonucleotide primer and a DNA template. Preparations comprising the DNA polymerase should be relatively free of contaminating agents with DNase or RNase activities. Additionally, the DNA polymerase should be capable of remaining stable and active under the DNA conversion reaction conditions. The particular DNA polymerase that is used will depend on whether the DNA conversion reaction is part of an RNA or DNA amplification reaction, as set forth hereinafter.

The DNA conversion reaction comprises the necessary concentrations of cofactors and nucleoside triphosphates for DNA synthesis using the particular DNA polymerase. The DNA conversion reaction is performed under the conditions of pH, ionic strength and temperature that are appropriate to the enzyme which is used. Such reaction conditions are known to those skilled in the art.

In one embodiment of this process, the DNA conversion reaction comprises part of an RNA amplification reaction, for example NASBA. In this embodiment, the DNA templates are provided by the reverse transcription step of the RNA amplification reaction and the DNA polymerase is preferably the same enzyme as the reverse transcriptase. Subtractive amplification with NASBA uses the reverse transcriptase from avian myeloblastosis virus (AMV) in the RNA amplification reaction, though another retroviral polymerase could be used. An RNA amplification process, such as NASBA, does not require the promoter template to function also as a primer. It is even preferable that the promoter template used in this embodiment is actually blocked to avoid the formation of primer-dimers from any primer extension following self-annealing. The various methods in the art for blocking a primer generally include substitution of the terminal 3'-OH with another chemical moiety.

In another embodiment of this process, the DNA conversion reaction is performed within a DNA amplification reaction. In this embodiment, the DNA conversion reaction medium further comprises a first primer, and the promoter template therein further comprises a second primer under conditions such that the second primer hybridizes to the DNA templates and is extended using the DNA polymerase to form double-stranded DNA templates, upon which a cycle ensues wherein: i) the complementary DNA strands of each double-stranded DNA template are separated; ii) the first primer and the second primer each hybridize to their complementary DNA strands; and iii) the primers are then extended using the DNA polymerase to form double-stranded DNA templates, thereby forming DNA templates with functional double-stranded promoters. In effect, the DNA conversion reaction is replaced with a modified DNA amplification reaction.

In another embodiment, a portion of the reverse transcription reaction is first added to a DNA amplification reaction medium comprising the first primer, a second primer and a DNA polymerase under conditions such that the second primer hybridizes to the DNA templates and is extended using the DNA polymerase to form double-stranded DNA templates, and the complementary strands of each double-stranded DNA template are separated, upon which a cycle ensues wherein: i) the first primer and the second primer each hybridizes to their complementary DNA strands; ii) the primers are then extended using the DNA polymerase to form double-stranded DNA templates; and iii) the complementary DNA strands of each double-stranded DNA template are separated; and thereafter a portion of the DNA amplification reaction is added to the DNA conversion reaction, hence providing DNA templates.

The DNA amplification reaction may be the polymerase chain reaction ("PCR"), wherein the complementary DNA strands of the double-stranded DNA are separated by adjusting the reaction conditions to cause denaturation. The DNA polymerase that is used for DNA conversion and amplification in PCR should be preferably capable of remaining stable under the denaturation and hybridization conditions of PCR. Such DNA polymerases may be prepared from a thermophilic bacteria, such as *Thermus aquaticus, Thermus thermophilus* or *Pyroccocus furigenes*. The reaction medium comprises the necessary concentrations of cofactors and nucleoside triphosphates for DNA synthesis using the particular DNA polymerase. PCR is also performed under the conditions of pH, ionic strength and temperature that are appropriate to the enzyme which is used. Each step of strand separation, primer hybridization and primer extension are controlled using a thermal cycling device, whereby each reaction temperature is maintained for a fixed duration, and each cycle of three steps may be repeated a predetermined number of times. PCR reaction conditions suitable to the practice of this invention are known to those skilled in the art U.S. Pat. No. 4,683,202 to Mullis, et al., "Specific Enzymatic Amplification of DNA In Vitro: The Polymerase Chain Reaction", Cold Spring Harbor Symp. Quant. Biol., Vol. 51, pp 263–273, (1986).

Alternatively, the DNA amplification reaction may be strand displacement amplification, wherein the reaction medium further comprises a restriction endonuclease and the first and second primers further comprise recognition sites for the restriction endonuclease under conditions such that the restriction endonuclease nicks the primers of the double-stranded DNA and the complementary DNA strands of the double-stranded DNA are separated by the DNA polymerase extending the nicked primers to displace the complementary DNA strands. The restriction endonuclease is one which can cut the unmodified primers but cannot cut the modified DNA extension product. The choice of DNA polymerase and restriction endonuclease depends on the temperature which is maintained throughout the SDA reaction. At a relatively moderate temperature, for example 41° C., the Klenow fragment of *E. coli* DNA polymerase I and the restriction endonuclease Hinc II may be used. Optimal practice of SDA generally uses a more elevated reaction temperature. The SDA reaction comprises the necessary concentrations of cofactors and nucleoside triphosphates for DNA synthesis using the particular DNA polymerase. In particular the SDA reaction contains an a-thioated nucleoside triphosphate, such as ($\alpha$-thiol)dATP, replacing the natural nucleoside triphosphate, such as dATP. The SDA reaction is performed under the conditions of pH, ionic strength and temperature that are appropriate to the enzymes which are used. SDA reaction conditions suitable to the practice of this invention are known to those skilled in the art U.S. Pat. No. 5,455,166 to Walker, et al., "A Chemiluminescent DNA Probe Test Based on Strand Displacement Amplification", Molecular Methods for virus Detection, pp. 329–349, (1995).

The fourth step of the process comprises a transcription reaction, wherein DNA templates with attached promoters from the DNA conversion reaction are provided in a medium comprising an RNA polymerase under conditions such that the RNA polymerase recognizes the double-stranded promoter and synthesizes copies of the target RNA sequences from the DNA template. In the preferred embodiment, the DNA templates with functional double-stranded promoters are provided by adding a portion of the DNA conversion reaction to the transcription reaction. In one embodiment of this process the transcription reaction comprises part of an RNA amplification method, for example, NASBA.

The RNA polymerase which is used in this invention may be any enzyme capable of binding to a particular DNA sequence called a promoter and specifically initiating RNA synthesis at a defined initiation site within close proximity to the promoter. Preparations comprising the DNA polymerase should be relatively free of contaminating agents with DNase or RNase activities. In addition the RNA polymerase should be capable of synthesizing several copies of RNA per functional copy of DNA template in a reasonable period of time. In the preferred embodiment, the bacteriophage T7 RNA polymerase is used. In addition other bacteriophage RNA polymerases, such as phage T3, phage $\phi$II, Salmonella phage sp6, or Pseudomonas phage gh-1, may be used. It is understood by those skilled in the art that the use of alternative RNA polymerases will require changes to the sequence of the promoter template according to the specificity of the particular RNA polymerase.

The transcription reaction comprises the necessary concentrations of cofactors and nucleoside triphosphates for RNA synthesis using the particular RNA polymerase. The transcription reaction is performed under the conditions of pH, ionic strength and temperature that are appropriate to the enzyme which is used. Such reaction conditions are known to those skilled in the art.

In one embodiment of the process, the reverse transcription, DNA conversion and transcription reactions together comprise an RNA amplification reaction, wherein tester RNA sequences are provided in a medium comprising a first primer, a promoter template, a reverse transcriptase, a DNA polymerase and an RNA polymerase under conditions such that the tester RNA sequences hybridize to the first primer and provide templates for synthesis of DNA templates by extension of the annealed first primer using the reverse transcriptase, thereby forming RNA:DNA hybrids, the RNA strands of which are degraded; the DNA templates hybridize to the promoter template and are extended using the DNA polymerase, thereby forming DNA templates each with a functional double-stranded promoter; and the RNA polymerase recognizes each double-stranded promoter and synthesizes from the DNA templates copies of the target RNA sequences. The DNA polymerase of the RNA amplification process may be a reverse transcriptase.

In the preferred embodiment, the RNA amplification process is cyclic, wherein the target RNA sequences from one round of the RNA amplification reaction may provide in the same reaction medium tester RNA sequences for a subsequent round of RNA amplification. The RNA amplification reaction comprises the necessary concentrations of cofactors and nucleoside triphosphates for RNA and DNA synthesis using the particular RNA and DNA polymerases described herein. The RNA amplification reaction is performed under the conditions of pH, ionic strength and temperature that are appropriate to the enzymes which are used. In the preferred embodiment, in a process commonly referred to as NASBA, the RNA amplification reaction medium further comprises a ribonuclease, an RNase H, that hydrolyzes the RNA of an RNA:DNA hybrid under conditions such that the RNA tester sequences forming hybrids with the DNA templates are degraded. NASBA reaction conditions suitable to the practice of this invention are known to those skilled in the art Sooknanan, et al., "Detection and direct sequence identification of BCR-ABL mRNA in Ph[30] chronic myeloid leukemia", Experimental Hematology, Vol. 21, pp. 1719–1724, (1993). In the preferred embodiment, the tester RNA sequences are provided by adding a portion of the hybridization reaction comprising the tester RNA sequences that do not anneal to the driver sequences to the RNA amplification reaction.

For the purpose of further enrichment of target RNA sequences from a mixture of tester RNA sequences that did not effectively anneal to the driver nucleic acid sequences during hybridization, the process may be repeated using the target RNA sequences generated from one round of the process to provide the tester RNA sequences in a subsequent, preferably the next, round of the process. In the preferred embodiment, tester RNA sequences are provided by adding a portion of the transcription reaction comprising target RNA sequences from one round of the process to the hybridization reaction of a subsequent round of the process. For the embodiment of the process where the reverse transcription, DNA conversion and transcription reactions together comprise an RNA amplification reaction, the tester RNA sequences are provided by adding a portion of the RNA amplification reaction comprising target RNA sequences from one round of the process to the hybridization reaction of a subsequent round of the process.

Since the target RNA from one round of the subtractive amplification process can be used as tester RNA for a subsequent or the next round of the process, the initial step of the process becomes arbitrary, though the relative order of the four steps of the process is maintained. In the preferred embodiment of the process involving RNA amplification, the steps of the process have the following order: 1) the hybridization reaction; and an RNA amplification reaction comprising 2) the reverse transcription reaction; 3) the DNA conversion reaction; and 4) the transcription reaction. In the preferred embodiment of the process involving DNA amplification, the steps of the process have the following order: 1) the transcription reaction; 2) the hybridization reaction; 3) the reverse transcription reaction; and 4) a DNA amplification reaction comprising the DNA conversion reaction. In this embodiment, the hybridization reaction may further comprise an RNA polymerase, effectively combining the transcription and hybridization reactions. A mixture of DNA templates each with a functional double-stranded promoter is added to this combined transcription- hybridization reaction, under initial conditions such that the RNA polymerase recognizes each double-stranded promoter and synthesizes from the DNA templates copies of a mixture of RNA comprising target RNA sequences and each comprising terminal priming sequences, hence providing tester RNA sequences. Thereafter, the conditions are changed such that driver sequences hybridize with complementary tester sequences, the tester sequences that anneal to driver sequences being thereby rendered incapable of functioning as templates for nucleic acid synthesis.

It is further contemplated that a cyclic subtractive amplification process could be performed within a single homogeneous reaction, wherein the target RNA sequences from one round of the subtractive amplification may provide in the same reaction medium tester RNA sequences for a subsequent round of subtractive amplification. In this homogenous subtractive amplification reaction, the tester RNA sequences are provided in a medium comprising driver nucleic acid sequences, a first primer, a promoter template, a reverse transcriptase and an RNA polymerase under conditions such that driver sequences hybridize with complementary tester sequences, the tester sequences that anneal to driver sequences being thereby rendered incapable of functioning as templates for nucleic acid synthesis, the tester RNA sequences that do not anneal to the driver sequences hybridize to the first primer and provide templates for synthesis of DNA templates by extension of the annealed first primer using the reverse transcriptase, thereby forming RNA:DNA hybrids, the RNA strands of which are degraded, the DNA templates hybridize to the promoter template and are extended using the DNA polymerase, thereby forming DNA templates with functional double-stranded promoters, and the RNA polymerase recognizes the double-stranded promoter and synthesizes from each DNA template copies of the target RNA sequences. Thereafter, target RNA sequences from one round of subtractive amplification in the same reaction medium tester RNA sequences for a subsequent round of subtractive amplification. The driver nucleic acid sequences may be composed of DNA and the reaction medium may further comprise an RNase H, which would degrade tester RNA sequences that anneal to the driver DNA sequences or form a hybrid with the DNA templates.

It may be desirable, for purposes including cloning of the DNA products, to end the subtractive amplification process with the synthesis of double-stranded DNA templates. In this embodiment, the final round of the subtractive amplification process comprises: 1) a hybridization reaction, wherein the tester sequences are provided in a medium comprising driver sequences under conditions such that driver sequences hybridize with complementary tester sequences, the tester sequences that anneal to driver sequences being thereby rendered incapable of functioning as templates for nucleic acid synthesis; 2) a reverse transcription reaction, wherein tester sequences from the hybridization reaction are provided in a medium comprising a first primer and a reverse transcriptase under conditions such that the tester RNA sequences that do not anneal to the driver sequences hybridize to the first primer and provide templates for synthesis of DNA templates by extension of the annealed first primer using the reverse transcriptase, thereby forming RNA:DNA hybrids, the RNA strands of which are degraded; 3) a DNA duplexing reaction, wherein DNA templates from the reverse transcription reaction are provided in a medium comprising a DNA polymerase and a second primer under conditions such that the DNA templates hybridize to the second primer and provide templates for synthesis of double-stranded DNA templates by extension of the annealed second primer using the DNA polymerase.

The DNA duplexing reaction may be performed within a DNA amplification reaction, wherein the DNA duplexing reaction medium further comprises a first primer under conditions such that the second primer hybridizes to the DNA templates and is extended using the DNA polymerase to form double-stranded DNA templates, upon which a cycle ensues wherein: i) the complementary DNA strands of each double-stranded DNA template are separated; ii) the first primer and the second primer hybridize to their complementary DNA strands; and iii) the primers are then extended using the DNA polymerase to form double-stranded DNA templates.

The first primer that is used in the DNA amplification reactions and the DNA duplexing reactions described herein should be functionally equivalent to the first primer used in the reverse transcriptase reaction but may not necessarily be identical. It is contemplated that additional nucleotides or chemical moieties may be present on one or the other primer.

The double-stranded DNA templates of the duplexing reaction may be characterized by cloning and sequencing. The cloned DNA templates may be utilized as hybridization probes. The probes could take the form of double-stranded plasmid DNA, single-stranded phage or phagemid DNA, or single-stranded RNA transcripts. Alternatively, the characterized sequences may be used in the design of hybridization probes or amplification primers. In this manner, the characterized sequences may be used to identify or characterize a useful nucleic acid sequence. Additionally, the cloned DNA templates could be utilized for the preparation of tester RNA sequences by in vitro transcription, or for the preparation of driver nucleic acid sequences by methods described herein. These tester RNA sequences and driver nucleic acid sequences may be further utilized in the practice of subtractive amplification using tester or driver sequences that are derived from still another cell population.

EXAMPLE 1

Preparation of Driver DNA Sequences

Cellular RNA was prepared from KG-1 cells (ATCC NO. CCL246) using standard methods, and cDNA clones encoding the G-CSF receptor (G-CSFR) and the thrombopoeitin receptor (c-mpl) were amplified from the RNA preparation by RT-PCR using primers specific for the G-CSFR and c-mpl sequences, as set forth in Table 1. [Oligonucleotide primers and probes were synthesized on an Applied Biosystems instrument (Model 392–28) (Foster City, Calif.) and were purified by polyacrylamide gel electrophoresis.] Two PCR primers (SEQ. ID. NOs. 3 and 4) were used to amplify a 915-bp fragment of the G-CSFR cDNA sequence (from 241 to 1155 of Genbank Accession No. M59818 M38025) and create cloning sites for NsiI and HindIII. Four PCR primers (SEQ. ID. NOs. 5, 6, 7 and 8) were used to amplify 870- and 568-bp fragments of the c-mpl cDNA sequence (from 76 to 946 and 904 to 1471 of Genbank Accession No. M90103) and create cloning sites for NsiI and HindIII. The two c-mpl cDNA fragments were joined into a single 1414-bp fragment using an overlapping NheI site in the natural cDNA sequence. The PCR products for G-CSFR and c-mpl were digested with NsiI and HindIII and ligated into the PstI and HindIII sites of pT7T319u (Pharmacia). The resulting plasmids, pT7T3-G and pT7T3-M, were then used to prepare single-stranded driver DNA sequences for G-CSFR and c-mpl, respectively. Phagemid DNA of recombinants pT7T3-G and pT7T3-M were isolated according to the procedure supplied with the M13K07 helper phage (New England Biolabs). Each phagemid DNA was purified after SDS-lysis of the phage supernatant and extraction with phenol/chloroform, and quantified at A260 nm.

EXAMPLE 2

Preparation of Tester RNA Sequences

Specialized vectors were constructed for the cloning of cDNA and the preparation of tester RNA libraries. One of these, pCAT, was constructed by annealing and ligating together four synthetic oligonucleotides, as set forth in Table 2 (SEQ. ID. NOs. 9, 10. 11 and 12) to form a 108-bp fragment, which was ligated into the EcoRI and PstI sites of pUC19 (Pharmacia). A second vector, pCATman, was constructed by annealing and ligating together three synthetic oligonucleotides, as set forth in Table 2 (SEQ. ID. NOs. 12, 13 and 14) to form a 88-bp fragment, which was ligated into the EcoRI and NheI sites of pCAT. These vectors could be used for in vitro transcription with T7 RNA polymerase to generate RNA that can be amplified using Primer 1 (P1) (SEQ. ID. NO. 11) and Primer2 (P2) (SEQ. ID. NO. 12).

The vectors pCAT and pCATman were used in the construction of plasmids for the preparation of tester RNA sequences from cDNA subclones of G-CSFR and c-mpl. A 140-bp fragment of G-CSFR cDNA was prepared from the PCR products of the primers identified by SEQ. ID. NOs. 3 and 4, by digestion with StuI, blunt-end ligation of the phosphorylated linker 5' pCTAGCTAG 3', and digestion with PstI and NheI. The sequence of the 144-bp PstI-NheI fragment of G-CSFR cDNA is shown in SEQ. ID. NO. 15 (from nucleotides 37 through 168) and in SEQ. ID. NO. 16 (from nucleotides 29 through 168). Similarly, a 144-bp fragment of c-mpl cDNA was prepared from the PCR products of the primers identified by SEQ. ID. NOs. 5 and 6, by digestion with PstI and NheI. The sequence of the 169-bp PstI-NheI fragment of c-mpl cDNA is shown in SEQ. ID. NO. 17 (from nucleotides 37 through 197) and in SEQ. ID. NO. 18 (from nucleotides 29 through 197). The two PstI-NheI fragments were then ligated into the PstI and XbaI sites of pCAT. The resulting plasmids, p3-G and p4-M, were then used to prepare tester RNA sequences by in vitro transcription.

A standard transcription reaction contained 50 mM Tris (pH 8.5), 50 mM KCl, 8 mM MgCl$_2$, 1.5 mM ATP, 1.5 mM GTP, 1.5 mM, CTP, 1.5 mM UTP, 10 mM DTT, 500 ng plasmid DNA, 25 units ribonuclease inhibitor and 60 units T7 RNA polymerase in a final volume of 25 µL. Plasmid DNA from recombinants p3-G and p4-M were first digested with Hind III restriction endonuclease according to the supplier (New England Biolabs) prior to transcription. The components of each transcription reaction were assembled at room temperature and then incubated at 37° C. for 1 hour. Following transcription, 1 unit RQ DNase I was added to each reaction tube and incubation at 37° C. was continued for another 15 minutes. The reaction mixtures were desalted using Bio-gel P6 (BioRad) and the amount of each transcript quantified at A260 nm.

The vector pCATman was used for cloning the entire cDNA fragments from the PCR products of Example 1. The 930-bp NsiI-HindIII fragment of G-CSFR cDNA was ligated into the MluI and HindIII sites of pCATman using the oligonucleotide adapter 5° CGCGTGCA 3' to join the MluI and NsiI ends, to make the plasmid p5-G. Similarly, the 1414-bp NsiI-HindIII fragment of c-mpl was ligated into the MluI and HindIII sites of pCATman to make the plasmid p6-M.

EXAMPLE 3

Selective Enrichment of a Specific Nucleic Acid Sequence after one Round of Subtractive Amplification using RT-PCR Single-stranded driver DNA was prepared from the pT7T3-M phagemid according to Example 1, and tester RNAs were prepared from p3-G and p4M according to Example 2. A standard hybridization reaction contained 40 mM Tris-HCl (pH 8.0), 10 mM MgCl$_2$, 100 mM NaCl, 1 mM dithiothreitol (DTT), 1 unit thermostable ribonuclease H (Hybridase™; Epicentre Technologies), 0.8 pmol (5×10$^{11}$ molecules) single-stranded driver DNA and a tester RNA sample in a final volume of 40 µL. Single-stranded phagemid DNA from pT7T3-M was used as the driver DNA. Various tester RNA mixtures were prepared, with the concentration of p4-M RNA kept constant at 0.19 pmol (10$^8$ molecules) and the concentration of p3-G increased from 0.016 amol (10$^4$ molecules) to 0.16 pmol (10$^8$ molecules) in 10-fold increments (set B). As a control, pT7T3-M driver DNA was not added to a second set of identical hybridization reactions (set A). The components of the hybridization reactions were assembled at room temperature, heated at 75° C. for 2 minutes and then incubated at 65° C. for at least 60 minutes.

Meanwhile, the reagents for nucleic acid amplification using RT-PCR were prepared. Each standard RT-PCR reaction comprised a cDNA synthesis step followed by PCR amplification. The standard cDNA synthesis reaction contained 10 mM Tris-HCl (pH 8.3), 50 mM KCl, 6 mM MgCl$_2$, 1 mM dATP, 1 mM dGTP, 1 mM dCTP, 1 mM TTP, 33 nM Primer 2 and 50 units Maloney murine leukemia virus reverse transcriptase (M-MuLV RT) (Bethesda Research Labs.) in a final volume of 30 µL. In addition, each cDNA synthesis reaction contained a 4-µL aliquot of the nucleic acid from a hybridization reaction or just H$_2$O as a control.

Except for a 2-µL aliquot containing M-MuLV RT, the remaining cDNA synthesis reaction components and nucleic acid sample or H$_2$O were mixed at room temperature, heated at 65° C. for 2 minutes and placed in a 40° C.-water bath. After allowing the reactions to equilibrate at 40° C. for 2 minutes, a 2-µL aliquot containing the M-MLV RT was added to each reaction tube and incubation at 40° C. continued for a further 30 minutes. Next, the tubes were transferred to a thermal-cycler (MiniCycler™; MJ Research) where they were heated at 99° C. for 5 minutes and then held at 85° C., during which time, a 70-µL aliquot of a PCR-mixture containing 10 mM Tris-HCl (pH 8.3), 50 mM KCl, 0.2 µM Primer 1, 0.2 µM Primer 2 and 1.5 units Taq polymerase (BMC) was added to each reaction tube. PCR amplification was initiated with the following profile: 94° C. for 1 minute, followed by 40 cycles of 94° C. for 40 seconds, 55° C. for 40 seconds and 72° C. for 30 seconds, and finally, 72° C. for 15 minutes.

The amplification products contained in a 5-µL aliquot of each amplification reaction were analysed by agarose gel electrophoresis and Southern blot hybridization Sambrook, et al., "Dot and Slot Hybridization of RNA", Molecular Cloning: A Laboratory, pp. 7.53–7.55, (1989) The Southern blot membrane was hybridized with [5-$^{32}$P] oligonucleotide probes specific to either p3-G amplicons (SEQ. ID. NO. 19) or p4-M amplicons (SEQ. ID. NO. 20).

The amplified products contained in those reactions to which no pT7T3-M driver DNA was added simply represented co-amplification of the different ratios of p3-G and p4-M RNA transcripts contained in the various mixtures. The p4-M amplicon was visible in all of the reactions (FIG. 1; Lanes A2–6), whereas the p3-G amplicon was only seen in those reactions where the p4-M RNA concentration was no higher than 1000× that of p3-G (Lanes A2–5).

However, when similar RNA mixtures were subjected to the subtraction process using pT7T3-M driver DNA, p4-M amplicons were no longer visible in the reaction that contained similar amounts of p3-G and p4-M transcripts at the start (Lane B2), and only gradually became apparent as the amount of the input p3-G RNA was decreasing (Lanes B3–6). More dramatic, however, was the relative increase in the levels of p3-G amplicons in the various mixtures (Lanes B2–6) including the reaction where essentially no p3-G amplicon was seen in the absence of driver DNA (Lanes A6 vs B6). Infact, in the latter reaction, the relative amounts of the p4-M and p3-G amplicons appeared to be the same after one round of subtractive amplification. Neither p3-G nor p4-M sequences were seen in the reaction where water was added instead of a nucleic acid sample (Lane 1). These results clearly demonstrated significant enrichment of the p3-G sequence following the inactivation of p4-M RNA by its complementary pT7T3-M driver DNA.

In FIGS. 1-I and 1-II, the following lanes contain the following materials:
1—no added template
2—10$^8$ p4-M and 10$^8$ p3-G RNA molecules
3—10$^8$ p4-M and 10$^7$ p3-G RNA molecules
4—10$^8$ p4-M and 10$^6$ p3-G RNA molecules
5—10$^8$ p4-M and 10$^5$ p3-G RNA molecules
6—10$^8$ p4-M and 10$^4$ p3-G RNA molecules
A—minus driver DNA
B—plus pT7T3-M driver DNA

EXAMPLE 4

Selective Enrichment of a Specific Nucleic Acid Sequence after Two Rounds of Subtractive Amplification using RT-PCR The amplified products of a first-round subtractive amplification reaction corresponding to lane B6 of FIG. 1 in Example 3 were serially diluted in 100-fold increments. Because RNA is required to facilitate the subtractive amplification process and since PCR generates only DNA, the PCR amplicons must be first transcribed in order to provide tester RNA for the second-round of subtractive amplification. Thus, a transcription reaction was coupled to the standard hybridization reaction. A standard coupled transcription-hybridization reaction contained 40 mM Tris-HCl (pH 7.5), 50 mM KCl, 15 mM MgCl$_2$, 1.5 mM ATP, 1.5 mM GTP, 1.5 mM CTP, 1.5 mM UTP, 5 mM DTT, 60 units T7 RNA polymerase, 1 unit thermostable RNase H and 0.8 pmol driver DNA in a final volume of 25 µL. In addition, each reaction contained 2.5 µL of either the 10$^{-4}$ or 10$^{-6}$ dilution of the above mentioned first-round reaction or H$_2$O as a control. As an additional control, no driver DNA was added to an identical 10$^{-6}$ dilution of the reaction. The driver DNA used in this example was pT7T3-M phagemid DNA prepared according to Example 1. The reactions were incubated at 40° C. for 30 minutes and then at 65° C. for 60 minutes, after which the reaction tubes were transferred back to 40° C. and 2 minutes. Thereafter, 1 unit of RQ DNase I (Promega) was added to each tube, and incubation at 40° C. was continued for an additional 30 minutes.

Meanwhile, standard RT-PCR amplification reactions were prepared following the teaching of Example 3, using 2-µL aliquots of the coupled transcription-hybridization reactions as tester RNA. The amplification reactions and subsequent detection of the amplified materials were performed according to the teaching of Example 3.

Figure 2:
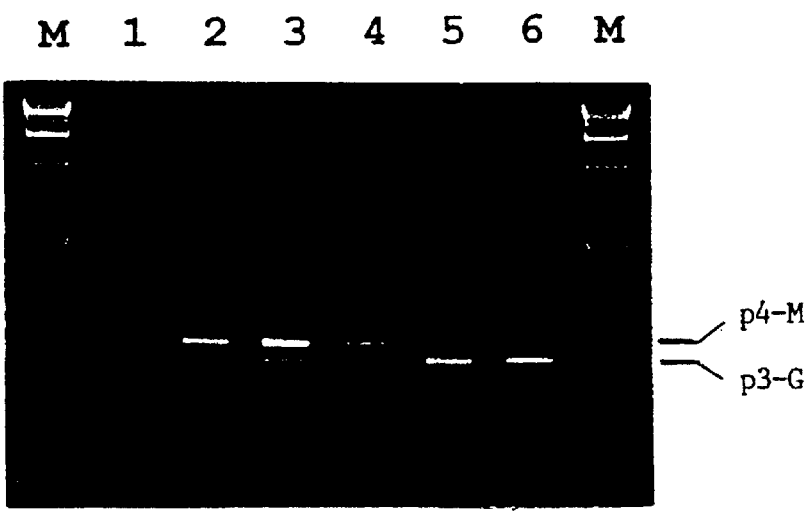
FIG. 2 shows agarose gel electrophoretic analysis of the products of the first and second rounds of subtractive amplification using PCR, where (I) is a photograph of the products detected by ethidium bromide staining, and (II) is an autoradiogram of the products detected by blot hybridization to radiolabeled oligonucleotide probes.
Figure 2:

The results showed no significant difference in the amounts of p3-G and p4-M amplicons upon re-amplification of the first-round reaction product without further subtraction with driver DNA (FIGS. 2-I and -II; Lanes 3 vs 4). However, following second-subtraction, the p3-G sequence was predominantly amplified in both dilutions of the said first-round reaction sample (FIGS. 2-I, -II; Lanes 5–6). In fact, p4-M amplicons were no longer visible in the re-amplified second-round samples based on the ethidium bromide stained agarose gel (FIG. 2-I; Lanes 5–6). Thus, two rounds of subtractive amplification appeared to have worked well for the selective enrichment of a unique nucleic acid sequence using RT-PCR.

In FIGS. 2-I and 2-II, the following lanes contain the following materials:

1—no added template
2—$10^8$ p4-M and $10^4$ p3-G RNA molecules minus driver DNA
3—$10^8$ p4-M and $10^4$ p3-G RNA molecules plus driver DNA
4—$10^{-4}$ dilution of #3 minus driver DNA
5—$10^{-4}$ dilution of #3 plus driver DNA
6—$10^{-6}$ dilution of #3 plus driver DNA

EXAMPLE 5

Selective Enrichment of a Specific Nucleic Acid Sequence after One Round of Subtractive Amplification using NASBA Single-stranded driver DNA was prepared from the pT7T3-G phagemid according to Example 1, and tester RNAs were prepared from p3-G and p4-M according to Example 2. Standard hybridization reactions were prepared following the teaching of Example 3, using pT7T3-G as phagemid. In this example, various tester RNA mixtures were prepared, with the concentration of p3-G RNA kept constant at 0.16 fmol ($10^8$ molecules) and the concentration of p4-M RNA increased from 0.019 amol ($10^4$ molecules) to 0.19 fmol ($10^8$ molecules) in 10-fold increments (set B). As a control, pT7T3-G driver DNA was not added to one set of comparable hybridization reactions (set A). The hybridization reactions were incubated following the teaching of Example 3.

Meanwhile, the reagents for the RNA amplification (NASBA) reactions were prepared. Each standard NASBA reaction contained 40 mM Tris-HCl (pH 8.5), 12 mM MgCl$_2$, 50 mM KCl, 10 mM DTT, 2 mM ATP, 2 mM CTP, 2 mM GTP, 2 mM UTP, 1 mM dATP, 1 mM dCTP, 1 mM dGTP, 1 mM TTP, 15% (v/v) dimethyl sulfoxide, 100 μg/mL BSA, 8 units avian myoblastosis virus reverse transcriptase (AMV RT) (Molecular Genetics Resources), 0.1 unit E. coli RNase H (Pharmacia), 40 units T7 RNA polymerase (Pharmacia), 12.5 units ribonuclease inhibitor (Pharmacia), 0.04 μM Primer 1 and 0.04 μM Primer 2 in a final volume of 25 μL. In addition, each standard NASBA reaction contained a 2-μL aliquot of the nucleic acid sample from a hybridization reaction or just H$_2$O as a control.

Except for a 2-μL aliquot of enzyme mixture comprising AMV RT, T7 RNA polymerase, E. coli RNase H and ribonuclease inhibitor, the remaining NASBA reaction components and nucleic acid sample or H$_2$O for each reaction were mixed at room temperature, heated at 65° C. for 2 minutes and then transferred to a water bath at 40° C. After 2 minutes at 40° C., 2 μL of the enzyme mixture was added to each reaction tube. Incubation of the reactions was continued at 40° C. for 90 minutes.

The amplification products contained in a 5-μL aliquot of each amplification reaction was analysed by agarose gel electrophoresis and by Northern blot hybridization analysis Sooknanan, et al., "Nucleic Acid Sequence-Based Amplification", Molecular Methods for Virus Detection, pp. 261–285 (1995). The Northern blot membrane was hybridized following the teaching of Example 3.

Figure 3:
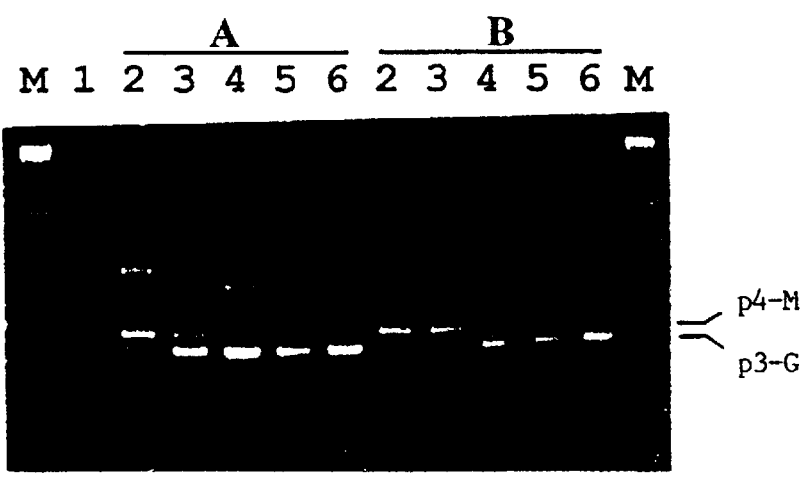
FIG. 3 shows agarose gel electrophoretic analysis of the products of subtractive amplification using NASBA, where (I) is a photograph of the products detected by ethidium bromide staining, and (II) is an autoradiogram of the products detected by blot hybridization to radiolabeled oligonucleotide probes.
Figure 3:
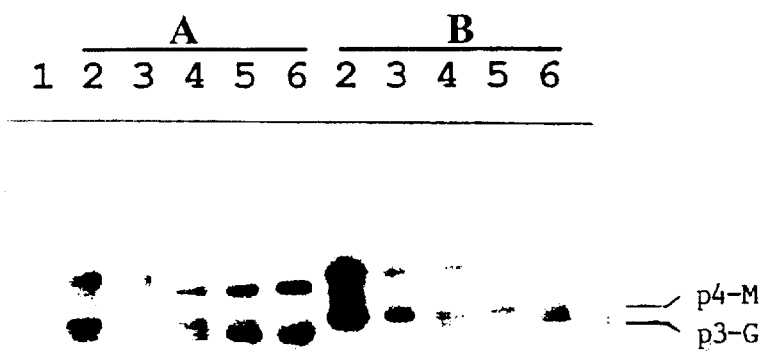

The amplified products contained in the reactions to which no pT7T3-G driver DNA was added represented simply the co-amplification of the different ratios of p3-G and p4-M RNAs (FIGS. 3-I, -II; Lanes A2–6). The p4-M amplicons were not visible in those reactions where the concentration of input p3-G RNA exceeded that of p4-M by at least 1000 fold (Lanes A5–6), whereas the p3-G amplicons were visible in all of the different mixtures (Lanes A2–6).

On the other hand, when the tester RNA mixtures were exposed to the pT7T3-G driver DNA, p4-M amplicons were readily visible even when the concentration of input p3-G RNA exceeded that of p4-M by $10^5$-fold (Lane B6). In addition, p3-G amplicons were no longer visible when the concentration of input p4-M was similar to or 10-fold lower than that of p3-G (Lanes B2–3). Neither p3-G nor p4-M amplicons were seen in the reaction to which water was added instead of a nucleic acid sample (Lane 1). These results clearly indicated that the p4-M sequence was selectively enriched as a direct result of the use of pT7T3-G driver DNA to inactivate the p3-G tester RNA.

In FIGS. 3-I and 3-II, the following lanes contain the following materials:

1—no added template
2—$10^8$ p3-G and $10^8$ p4-M RNA molecules
3—$18^8$ p3-G and $10^7$ p4-M RNA molecules
4—$10^8$ p3-G and $10^6$ p4-M RNA molecules
5—$10^8$ p3-G and $10^5$ p4-M RNA molecules
6—$10^8$ p3-G and $10^4$ p4-M RNA molecules
A—minus pT7T3-G driver DNA
B—plus pT7T3-G driver DNA

EXAMPLE 6

Selective Enrichment of a Specific Nucleic Acid Sequence after Two Rounds of Subtractive Amplification using NASBA After the first round of subtractive amplification, in the reaction corresponding to lane B5 of FIG. 3 in Example 5, the p4-M sequence appeared to be enriched to approximately the same level as the p3-G sequence. As a further demonstration, a second round of subtractive amplification was performed not only to further enrich the p4-M sequence, but also to reverse the enrichment process by re-selecting for the p3-G sequence. Thus, either single-stranded pT7T3-G or pT7T3-M driver DNA was added to identical hybridization reactions containing, as tester RNA mixtures, serial 100-fold dilutions of the amplified products of the selected reaction. Standard hybridization reactions were prepared following the teaching of Example 3, each containing 2-μL aliquots of the $10^{-4}$, $10^{-6}$ and $10^{-8}$ dilutions of the above mentioned first-round amplification reaction. In addition, a standard hybridization reaction containing 2 μL of the $10^{-8}$ dilution of the said first-round reaction did not receive any driver DNA as a control. The hybridization reactions were incubated following the teaching of Example 3, and then digested with 1 unit RQ DNase I endonuclease at 37° C. for 30 minutes prior to amplification.

Meanwhile, standard NASBA reactions were prepared following the teaching of Example 5, using 2-μL aliquots of the second-round hybridization reactions as tester RNA. The amplification reactions and subsequent detection of the amplified materials were performed according to the teaching of Example 5.

Figure 4:
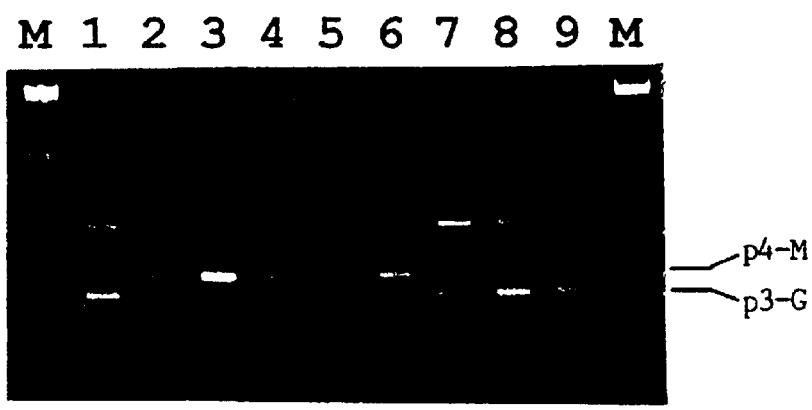
FIG. 4 shows agarose gel electrophoretic analysis of the products of the first and second rounds of subtractive amplification using NASBA, where (I) is a photograph of the products detected by ethidium bromide staining, and (II) is an autoradiogram of the products detected by blot hybridization to radiolabeled oligonucleotide probes.
Figure 4:
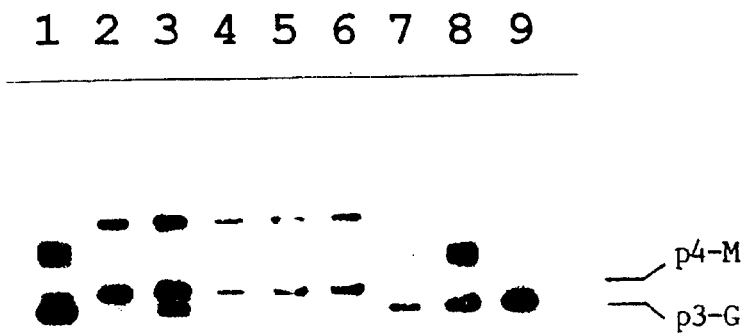

The product from the first round reaction (FIG. 4; Lane 2) when re-amplified in the absence of second-round subtraction resulted in the enrichment of both p3-G and p4M sequences equally (Lane 3). However, after the second-round subtraction with pT7T3-G driver DNA, the p4-M sequence was predominantly amplified in all three dilutions tested (Lanes 4–6). Similarly, when pT7T3-M driver DNA was used instead for subtraction, the p3-G sequence was predominantly amplified (Lane 7–9), reaching a level comparable to that of the primary reaction without subtraction (Lane 1).

Since there was no apparent difference in the amounts of second-round p4-M amplicon generated between the $10^{-4}$, $10^{-6}$ and $10^{-8}$ dilutions of the first round reaction, 0.8 pmol of driver DNA was sufficient to inactivate the complementary tester RNA sequence over a range of concentrations differing by as much as 10,000 fold. Also, the results clearly demonstrated that the subtractive amplification process was sequence-directed because the enrichment of a particular sequence was reversible depending on the sequence of the driver DNA used for subtraction. Overall, two rounds of the subtractive amplification process were sufficient to enrich a unique sequence (p4-M) from one of a minor species to clearly the more dominant species.

In FIGS. 4-I and 4-II, the following lanes contain the following materials:
1—$10^8$ p3-G and $10^5$ p4-M RNA molecules minus driver DNA
2—$10^8$ p3-G and $10^5$ p4-M RNA molecules plus driver DNA
3—$10^{-8}$ dilution of #2 minus driver DNA
4—$10^{-4}$ dilution of #2 plus pT7T3-G driver DNA
5—$10^{-6}$ dilution of #2 plus pT7T3-G driver DNA
6—$10^{-8}$ dilution of #2 plus pT7T3-G driver DNA
7—$10^{-4}$ dilution of #2 plus pT7T3-M driver DNA
8—$10^{-6}$ dilution of #2 plus pT7T3-M driver DNA
9—$10^{-8}$ dilution of #2 plus pT7T3-M driver DNA

EXAMPLE 7

Selective Enrichment of a Specific Nucleic acid Sequence using NASBA for the First-round and RT-PCR for the Second-round of Subtractive Amplification The hybridization reactions described in Example 6 were used as tester RNA for the second-round subtractive amplification using RT-PCR. The RT-PCR reactions were performed following the teaching of Example 3. The products contained in a 5-μL aliquot of each amplification reaction were analysed by agarose gel electrophoresis and Southern blot hybridization analysis following the teaching of Example 3.

Figure 5:
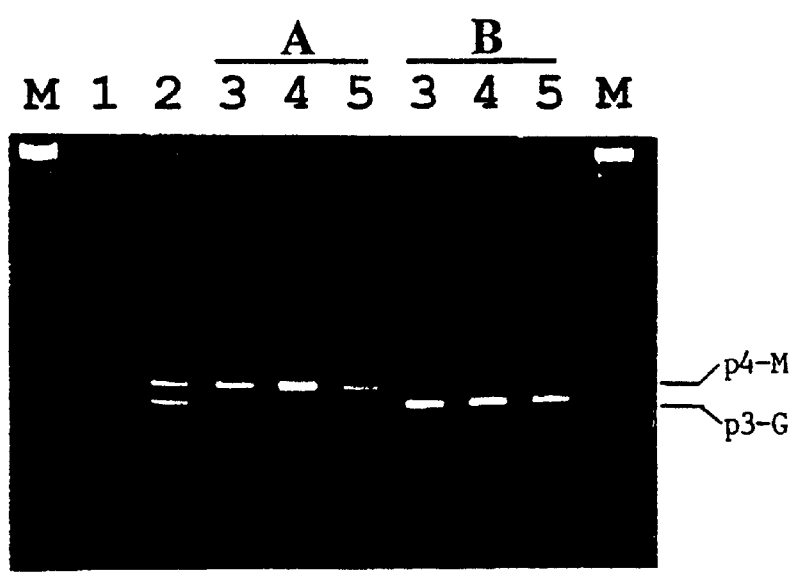
FIG. 5 shows agarose gel electrophoretic analysis of the products of a second round of subtractive amplification using PCR following a first round of subtractive amplification using NASBA, where (I) is a photograph of the products detected by ethidium bromide staining, and (II) is an autoradiogram of the products detected by hybridization to radiolabeled oligonucleotide probes.
Figure 5:

The second-round RT-PCR reaction without added driver DNA resulted in essentially equal amounts of p3-G and p4-M amplicons (FIG. 5-I, -II; Lane 2), which was similar to the first-round NASBA reaction (FIG. 3-I; Lane B5). However, after second-round subtractive amplification with pT7T3-G driver DNA, the p4-M sequence was significantly enriched in all three of the dilutions of the said first-round sample (FIGS. 5-I, -II; Lanes A3–5). The three dilutions ($10^{-4}$, $10^{-6}$ and $10^{-8}$) represented an increase in the driver:tester ratio of at least 10,000-fold. Thus, if at all expected, the p3-G amplicons will be the least efficiently subtracted in the lowest dilution of the first-round sample, and indeed, a trace of p3-G amplicons was still visible in this sample after re-amplification (Lane A3).

When the reciprocal second-round subtraction was performed with pT7T3-M driver DNA, the p3-G sequence was predominantly amplified instead for all three of the dilutions tested (Lanes B3–5). Interestingly, no p4-M amplicons were visible in the case of the least diluted sample (Lane B3) compared to the same dilution with pT7T3-G driver DNA. This observation suggested that the p4-M RNA may have been more efficiently inactivated than the p3-G RNA during the hybridization reaction.

These results clearly indicate that the amplified products of a first-round subtractive amplification process using NASBA can also be readily enriched in a second-round subtractive amplification reaction using RT-PCR. In fact, it should also be possible to perform second-round NASBA starting from the product of a first-round RT-PCR reaction by following the teaching of Example 4.

In FIGS. 5-I and 5-II, the following lanes contain the following materials:
1—no added template
2—$10^{-8}$ dilution of the first-round NASBA minus driver DNA
3—$10^{-4}$ dilution of the first-round NASBA plus driver DNA
4—$10^{-6}$ dilution of the first-round NASBA plus driver DNA
5—$10^{-8}$ dilution of the first-round NASBA plus driver DNA
A—pT7T3-G driver DNA
B—pT7T3-M driver DNA

EXAMPLE 8

RNase H -dependent and -independent Inactivation of Tester RNA Sequences

A sample of a first-round subtractive amplification reaction digested with RQ DNase I, as described in Example 4, was diluted $10^8$-fold. Five standard hybridization reactions minus RNase H were prepared each containing 2 μL of the $10^{-8}$ dilution of the said reaction. In addition, pT7T3-M driver DNA was added to four of the five reactions and two of these four reactions received thermostable RNase H. All reactions were hybridized following the teaching of Example 3.

Of the two reactions containing driver DNA and no RNase H, one was digested with RQ DNase I following hybridization and prior to amplification. Also, one of the two reactions containing driver DNA and RNase H was similarly digested. Samples of the different hybridization reactions were then enriched using either RT-PCR or NASBA performed following the teachings of Examples 3 and 5, respectively.

The amplification products of the RT-PCR reactions were analysed by agarose gel electrophoresis and Southern blot hybridization (FIGS. 7A-I, -II), following the teaching of Example 3, whereas the amplification products contained in 5-μL aliquots of the NASBA reactions were serially diluted and analyzed by slot-blot hybridization Sambrook, et al., "Dot and Slot Hybridization of RNA", Molecular Cloning: A Laboratory, pp. 7.53–7.55, (1989),(FIGS. 7B-I, -II), following the teaching of Example 5.

Figure 7:
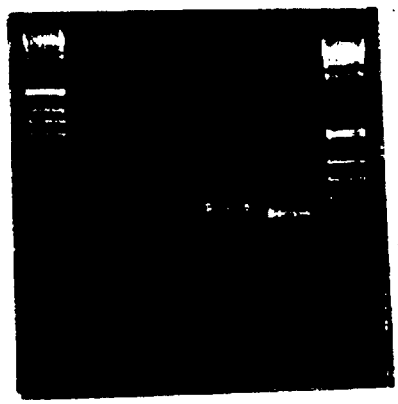
FIG. 7 shows agarose gel electrophoretic analysis of the products of transcription reactions of cDNA clones which were adapted with a P2 primer, where (I) is a photograph of the products detected by ethidium bromide staining, and (II) is an autoradiogram of the products detected by blot hybridization to radiolabeled oligonucleotide probes.
Figure 7:
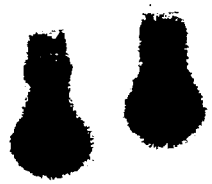

The amplified products of the second-round RT-PCR or NASBA reaction which did not receive any driver DNA contained essentially similar amounts of p3-G and p4-M amplicons as expected (FIGS. 7 A- and B-I, -II; Lane 2). The reactions containing just pT7T3-M driver DNA in the hybridization reaction (i.e. no RNase H), however, showed a significant increase in the level of the p3-G amplicon over the p4-M amplicon (FIGS. 7 A- and B-I, -II; Lane 3). Based on this result, simply annealing the p4-M RNA to its complementary driver DNA during the hybridization reaction was sufficient to block amplification of the RNA in the subsequent RT-PCR reaction.

This conclusion was further supported by results from another reaction containing driver DNA without RNase H that was digested with DNase I prior to re-amplification. In this reaction, the hybridization process appeared to have been reversed as a result of the DNase I treatment because both p3-G and p4-M were once again re-amplified to similar levels for both RT-PCR and NASBA (FIGS. 7 A- and B-I, -II; Lane 4). Essentially, the DNase I treatment destroyed the DNA of the RNA:DNA hybrid, and in so doing, the hybridized RNA was released to be amplified.

Conversely, when driver DNA and RNase H are present in the hybridization reaction, the RNA of a RNA:DNA hybrid would become hydrolyzed. Consequently, DNase I treatment of such a reaction should not reverse the hybridization process, whereby the RNA can once again be amplified. Thus, when this was the case, the p3-G sequence was preferentially enriched over p4-M in either RT-PCR or NASBA despite the DNase I digestion (FIGS. 7 A- and B-I, -II, Lanes 5–6).

Furthermore, the use of RNase H appears to also increase the efficiency of the subtraction process. That is, a minor band corresponding to the p4-M amplicon was visible after RT-PCR re-amplification of a sample not treated with RNase H compared to a similar sample containing RNase H (FIGS. 7A-I, -II; Lane 3 vs Lane 5). Similarly, the slot-blot results for comparable NASBA reactions showed a greater than ten-fold increase in efficiency when RNase H was used (FIG. 7B-I; Lanes 3 vs 5). The increased efficiency with RHase H is most likely due to multiple rounds of hybrid formation and degradation of the hybridized RNA during the hybridization reaction. Thus, the use of RNase H is not absolutely essential for enablement of the subtractive amplification process. In FIGS. 7 A- and B-I, -II, the following lanes contain the following materials,
1—no added template
2—$10^{-8}$ dilution of sample minus driver DNA
3—$10^{-8}$ dilution of sample plus driver DNA
4—$10^{-8}$ dilution of sample plus driver DNA plus DNase I
5—$10^{-8}$ dilution of sample plus driver DNA plus RNase H
6—$10^{-8}$ dilution of sample plus driver DNA, RNase H and DNase I

EXAMPLE 9

Subtraction Levels with and Without RNase H for RT-PCR and NASBA

Figure 6A:
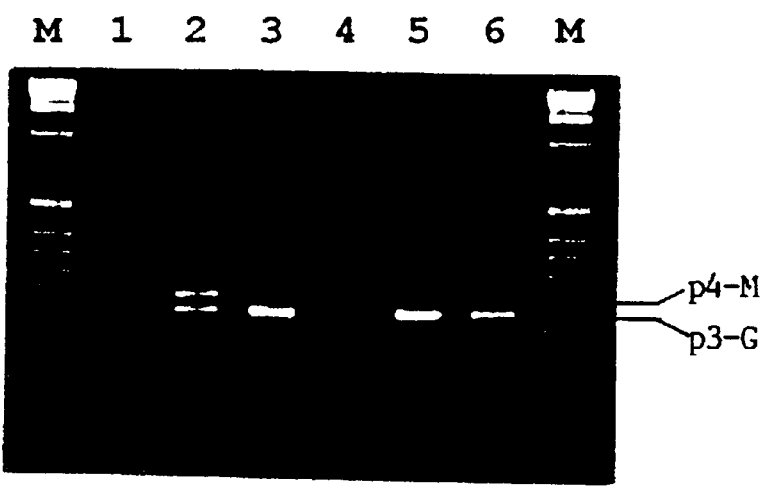
FIG. 6A shows agarose gel electrophoretic analysis of the products of subtractive amplification, wherein the hybridization reaction was variously treated with RNase H and/or DNase I before amplification using PCR, where (I) is a photograph of the products detected by ethidium bromide staining, and (II) is an autoradiogram of the products detected by blot hybridization to radiolabeled oligonucleotide probes.
Figure 6B:
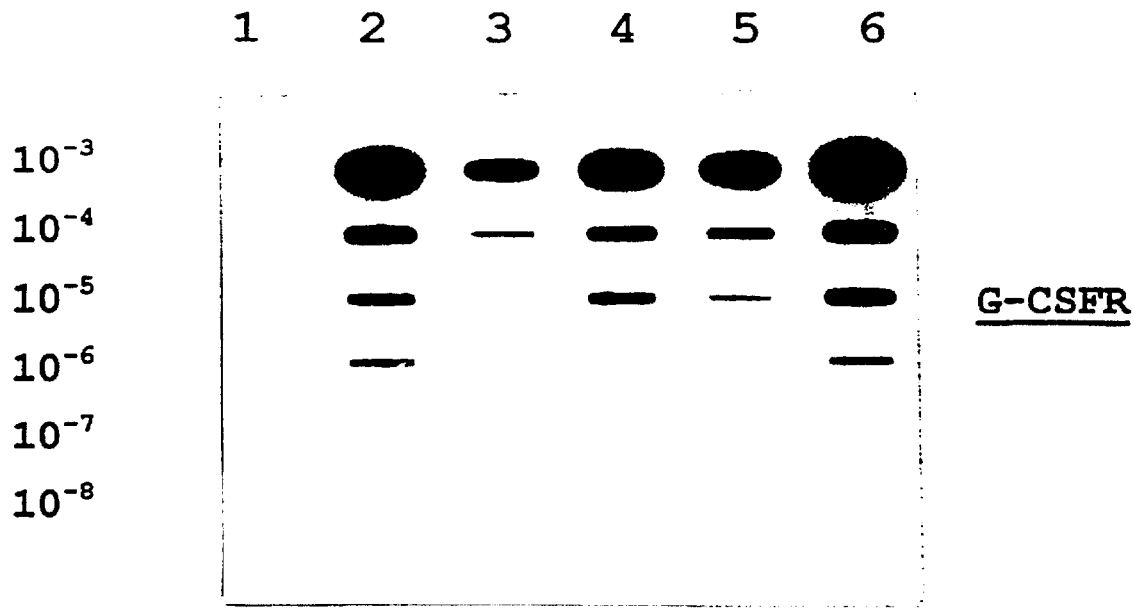
FIG. 6B shows autoradiograms of slot blot hybridization analysis of the products of subtractive amplification, wherein the hybridization reaction were variously treated with RNase H and/or DNase I before amplification using NASBA, where the products were detected by hybridization to probes specific to either (I) G-CSFR or (II) c-mpl sequences.
Figure 6B:
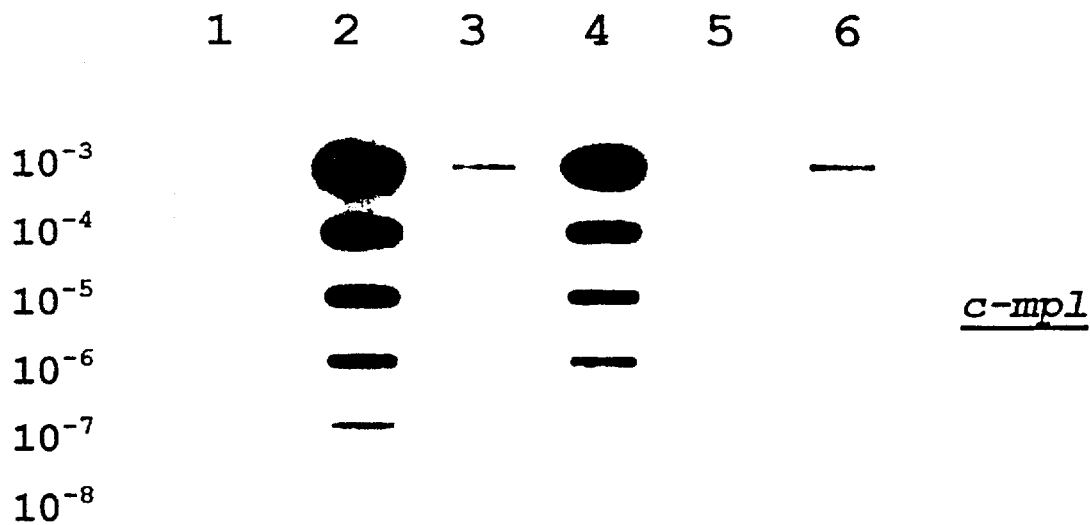

The levels of subtraction obtained with driver DNA alone or in combination with RNase H for samples #3 and #5 described in FIG. 6 in Example 8 were quantified by serial dilution and slot-blot analysis (Sambrook et al., 1989). Slot-blot membranes were hybridized with either of two $^{32}$P-labelled probes (SEQ. ID. NO. 3 and 4). The hybridized membranes were then dissected into individual slots and the radioisotope contained in each slot was measured in a scintillation counter. Based on the ratios of p3-G to p4-M amplicons obtained after hybridization for each sample, the levels of enrichment, and thus the relative subtraction efficiencies, were determined.

The presence of RNase H in the standard subtractive amplification reaction resulted in a 3- to 4-fold enrichment of the tester sequence in either NASBA or RT-PCR (Table 3). The improvement in subtraction with RNase H is attributed to multiple rounds of degradation of the RNA of a RNA:DNA tester-driver complex by RNase H because the same driver DNA can repeatedly bind a new RNA molecule once the previous RNA molecule has been degraded. The ensuing cycles of hybrid formation and degradation of the RNA will increase the efficiency of subtraction compared to the single hybridization-inactivation event with only driver DNA. These results confirm those of Example 8, in that the subtractive amplification process operates independently of RNase H.

EXAMPLE 10

P2-adaptation of cDNA Clones

Plasmid DNA, isolated from cDNA-recombinants p5-G and p6-G, were digested to completion with restriction endonuclease Sau3Al (New England Biolabs), and 0.1 pmol of each was added to separate ligation reactions containing 50 mM Tris-HCl (pH 7.5), 10 mM $MgCl_2$, 1 mM ATP, 5 mM DTT, 1 mg/ mL BSA, 1 pmol Primer 2, 1 pmol P2-adaptor (SEQ. ID. NO. 21) and 2.5 units T4 DNA ligase (Bethesda Research Labs.) in a final volume of 20 $\mu$L. In addition, DNA ligase was omitted from a second set of similar reactions. The reaction components were assembled at room temperature, heated at 65° C. for 2 minutes and incubated at room temperature (~22° C.) for 60 minutes.

Next, standard transcription reactions were prepared, according to the teaching of Example 2, containing a final concentration of 15 mM $MgCl_2$ and 25% of a ligation reaction described above. After incubating the reactions at 37° C. for 60 minutes, 1 unit RQ DNase I was added to each and incubation was continued at 37° C. for 30 minutes. The RNA transcripts synthesized in each reaction were desalted and the concentration of each was measured at $A_{260nm}$. In addition, 10% of each transcription reaction was analyzed by native agarose gel eiectrophoresis and northern blot hybridization using $^{32}$P-labeled Primer 2 (SEQ. ID. NO. 12) as the probe.

The RNA transcripts from the reactions to which DNA ligase was added corresponded to the expected sizes for p5-G (105 nt) and p6-M (436 nt) (SEQ. ID. Nos. 24 and 25, Table 5), based on the location of the first Sau3Al site from the 5' end of the respective cDNA fragment and the length of the Primer 2 sequence (FIG. 7-I; Lanes 1 and 3). On the other hand, the reactions to which no DNA ligase was added produced RNA transcripts that were shorter in length, likely due to the absence of the Primer 2 sequence (Lanes 2 and 4). As expected, only the P2-adapted RNA transcripts hybridized to Primer 2 when used as the probe (Lanes 1 vs 2 and 3 vs 4). In addition, the P2-adapted RNA transcripts were amplifiable both by NASBA and RT-PCR with primers 1 and 2. In FIGS. 9-I and 9-II, the following lanes contain the following materials,
1—Sau3Al digested p5 DNA plus T4 DNA ligase
2—Sau3Al digested p5 DNA minus T4 DNA ligase
3—Sau3Al digested p6 DNA plus T4 DNA ligase
4—Sau3Al digested p6 DNA minus T4 DNA ligase
M1—M.W. marker for Lanes 1 and 2
M2—M.W. marker for Lanes 3 and 2

EXAMPLE 11

Application of the Subtractive Amplification Process to the P2-adapted RNA transcripts The P2-adapted transcripts for p5-G and p6-M recombinants prepared according to the teaching of Example 10 were serially diluted in $H_2O$. Standard hybridization reactions were prepared following the teaching of Example 3 with the exception that the tester RNA comprised various mixtures of the P2-adapted p5-G and p6-M in which, the concentration of p5-G RNA was kept constant at 1.7 amol ($10^6$ molecules) and the concentration of the p6-M RNA was increased from 0.016 amol ($10^4$ molecules) to 1.6 amol ($10^6$ molecules) in 10-fold increments (set B). As a control, the pT7T3-G driver DNA was not added to a second set of identical hybridization reactions (set A). The hybridization reactions were all incubated following the teaching of Example 3.

Meanwhile, standard RT-PCR reactions were prepared following the teaching of Example 3 with the exception that all components of each reaction was reduced by 50%. The amplification reactions and subsequent detection of the amplified materials were performed also following the teaching of Example 3 with the exception that the Southern blot was hybridized with [$5'^{32}p$] oligonucleotide probes (SEQ. ID. NO. 22 and SEQ. ID. NO. 23) specific to either the p5-G amplicons (SEQ. ID. NO. 24) or the p6-M amplicons (SEQ. ID. NO. 25).

Figure 8:
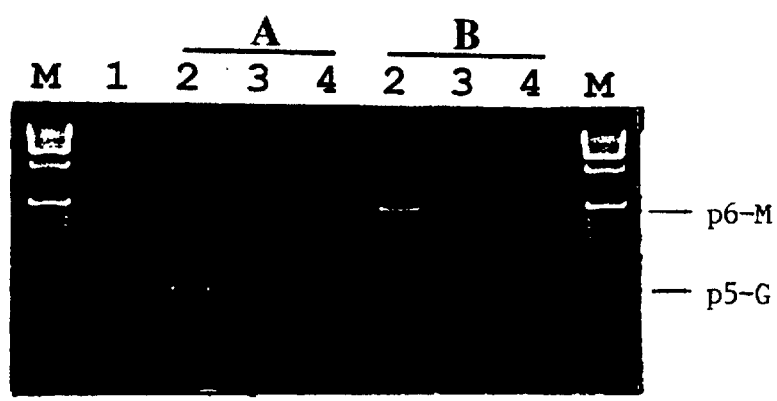
FIG. 8 shows agarose gel electrophoretic analysis of the products of subtractive amplification using PCR, where (I) is a photograph of the products detected by ethidium bromide staining, and (II) is an autoradiogram of the products detected by blot hybridization to radiolabeled oligonucleotide probes.
Figure 8:
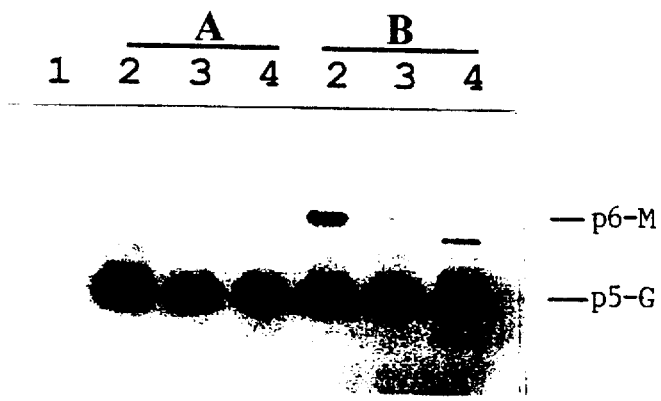

The relative co-amplification of the P2-adapted p5-G and p6-G transcripts independent of subtraction is shown in FIGS. 8 I, II; Lanes A2–4. Of the three mixtures of p5-G and p6-M transcripts, only the one containing an equal amount of each transcript produced both amplicons after RT-PCR amplification (Lane A2). For the other two mixtures, only the p5-G amplicon was seen (Lanes A3–4).

However, when similar RNA mixtures were subjected to subtraction with the pT7T3-G driver DNA, the copy number of the p6-M amplicon increased relative to that for p5-G in the mixture containing an equal amount of the two RNA transcripts (Lane B2). In addition, the p6-M amplicon was also now visible by both ethidium bromide staining and Southern hybridization in the reaction containing a 10-fold excess of p5-G RNA over p6-M RNA (Lane B3) and by Southern hybridization in the reaction containing a 100-fold excess of the p5-G RNA (Lane B4). The p5-G amplicon was still amplified in all the different RNA mixtures (Lanes B2–4). Neither p5-G nor p6-M sequences were seen in the reaction where water was added instead of a nucleic acid sample (Lane 1). These results clearly showed significant enrichment of the P2-adapted p6-M sequence following inactivation of the p5-G sequence with pT7T3-G driver DNA.

In FIGS. 8-I and 8-II, the following lanes contain the following materials,
1—no added template
2—$10^6$ p5-G and $10^6$ p6-M RNA molecules
3—$10^6$ p5-G and $10^5$ p6-M RNA molecules
4—$10^6$ p5-G and $10^4$ p6-M RNA molecules
A—minus driver DNA
B—plus T7T3-G driver DNA

EXAMPLE 12

Preparation of Tester RNA and Driver DNA Sequences

Cellular mRNA was prepared from $7.7 \times 10^7$ KG-1 cells using the Oligotex™ Direct mRNA kit (QIAGEN catalog #72041). The KG-1 cell pellet was resuspended in 0.3 mL of the supplied lysis buffer, and mRNA was purified as described in the QIAGEN handbook, following the additional mRNA enrichment protocol. The Time Saver cDNA synthesis kit (Pharmacia catalog #27-9262-01) was used to synthesize cDNA from 1 μg KG-1 mRNA, following the protocol that was provided with the kit. Replacing the oligo dT primer supplied in the kit was a bifunctional primer containing a $dT_{11}V$-3' sequence and a Not I recognition site as set forth in Table 6 (SEQ. ID. NO. 28). Briefly, the bifunctional primer was annealed to the KG-1 mRNA and was extended to form the first strand cDNA using M-MuLV RT. The oligoribonucleotides, which were generated by nicking the original mRNA strand with E. coli RNase H and remained annealed to the first strand cDNA, were extended to form the second strand of cDNA using E. coli DNA polymerase I. The resulting double-stranded cDNA was then ligated to phosphorylated linkers containing an Asc I recognition site (5'-pAGGCGCGCCT-3') using T4 DNA ligase. The double-stranded ligated cDNA was then digested with Asc I and Not I and purified from the excess linkers using a Sepharose CL-4B gel spin column.

Specialized vectors were constructed for the cloning of cDNA libraries and the preparation of tester RNA and driver DNA. One of these, p7, was constructed by digesting vector pCATman (set forth in Example 2) with Hind III, filling in the ends with Klenow DNA polymerase and recircularizing the blunt ends with T4 DNA ligase. This resulted in the formation of a second Nhe I site, flanking the Primer 2 (P2) sequence. This ligated intermediate was then digested with Nhe I and recircularized with T4 DNA ligase to obtain the vector p7, in which the P2 priming site had been excised. A second vector, p8, was constructed by annealing and ligating together three synthetic oligonucleotides as set forth in Table 2 (SEQ. ID. NOs. 12, 13 and 14), to form a 88-bp fragment, which was ligated into the EcoR I and Xba I sites of pT7T3/19u (Gibco BRL Life Technologies).

Following the teaching of this example, double-stranded cDNA adapted with Asc I and Not I ends was synthesized from 1 μg of rabbit globin mRNA (Gibco BRL Life Technologies). The rabbit globin cDNA was ligated into the Asc I and Not I sites of the p7 vector and used to transform E. coli DH5α (Gibco BRL Life Technologies). Upon screening of the transformants, two clones were selected. One was p7α, which contained a 528-bp cDNA fragment encoding rabbit α globin (from nucleotides 25 to 552 of GenBank Accession No. J00658), and the other was p7β, which contained a 414-bp cDNA fragment encoding rabbit β globin (from nucleotides 176 to 589 of GenBank Accession No. V00879). The β globin cDNA insert of p7β was excised with Asc I and Not I and ligated into the same sites of p8 to obtain the vector p8β.

Sequences from bacteriophage lambda were cloned into the p7β vector for generating target RNA sequences in the tester RNA mixture. Lambda DNA was digested with Mlu I and Sau3A I, and the resulting fragments were ligated into the Mlu I and BamH I sites of p7β. The following lambda DNA subclones were identified by screening the resulting transformants: p7λ43, containing a 43-bp fragment (from nucleotides 5506 to 5548); p7λ99, containing a 99-bp fragment (from nucleotides 5549 to 5647); and p7λ260, containing a 260-bp fragment (from nucleotides 15113 to 15372) [All nucleotide positions on lambda DNA are in reference to GenBank Accession No. J02459].

The double-stranded KG-1 cDNA adapted with Asc I and Not I ends, which was synthesized according to the teaching of this example, was ligated into the Asc I and Not I sites of the p7β and p8β vectors and used to transform E. coli DH5α and NM522 (Pharmacia), respectively. The plated colonies from each vector were pooled to obtain the tester (p7-L1) and driver (p8-L1) libraries of $6 \times 10^5$ and $4 \times 10^5$ transformants, respectively. Plasmid DNA was prepared from each pool of cells using the QIAprep kit (QIAGEN catalog #72041) and following the Miniprep protocol included with the kit. The completed libraries were characterized by colony-blot hybridization and restriction analysis of the pooled plasmid DNA. A 12S rRNA clone was identified in the p7-L1 library by probing with the radiolabeled probe OGS36 as set forth in Table 6 (SEQ. ID. NO. 29). To prepare a driver DNA for 12S rRNA, the 936-bp insert of p7-12S (from nucleotides 663 to 1598 of GenBank Accession No. J01415) was excised with Asc I and Not I, and ligated into the same sites of the p8 vector to generate p8-12S.

The p7-L1 library and the lambda DNA subclones were then used to make tester RNA. Plasmid DNA from the p7-L1 cDNA library and an equimolar mixture of three lambda clones (p7λ43, p7λ99 and p7λ260), were separately digested to completion with restriction endonuclease Sau3A I and adapted with Primer 3 (Table 6; SEQ. ID. NO. 30) using the P3-adapter (Table 6; SEQ. ID. NO. 31) following the teaching of Example 10. Each P3-adapted plasmid DNA preparation was used for the synthesis and preparation of tester RNA according to the teachings of Example 2 and Example 10. The RNA transcripts synthesized in each reaction were desalted and the concentration of each measured at $A_{260nm}$. The p8-L1 library was used to make single-stranded DNA driver. The p8-L1 plasmid DNA (16 μg) was digested with Not I in four equal 40-μL reactions each containing 1× TA Buffer [33 mM Tris-acetate (pH 7.8), 66 mM potassium acetate, 10 mM magnesium acetate and 0.5 mM DTT], 100 μg/mL bovine serum albumin and 50 units of Not I (New England Biolabs). The reactions were incubated at 37° C. for at least 2 h, and then heated at 65° C. for 15 min to inactivate the Not I enzyme. The Not I fragments of p8-L1 in each of the 40-μL reactions were dephosphorylated by adding 1 μL of 10× TA Buffer, 2.5 μL 100 mM $CaCl_2$ and 5 μL water; incubating at 30° C. for 5 min; adding 1.5 μL of 1 units/mL HK thermolabile phosphatase (Epicentre Technologies); and incubating at 30° C. for a further 4 h. The dephosphorylated Not I fragments of p8-L1 were then digested with Asc I in reactions made to 60 μL containing 10 mM EGTA, 1× TA Buffer and 20 units of Asc I (New England Biolabs). The reactions were incubated at 37° C. for at least 2 h, and then heated at 65° C. for 15 min to inactivate the Asc I enzyme. After pooling the four reactions, the p8-L1 fragments were purified by ultrafiltration using a moistened Amicon-30 filter and resuspended in 50 μL water. Finally, the 5'-phosphorylated strands of the Asc I-Not I fragments of p8-L1 (48 μL) were digested with λ-exonuclease in a 62.5-μL reaction containing 67 mM glycine-KOH (pH 9.3), 2.5 mM $MgCl_2$ and 9 units λ-exonuclease (Pharmacia). The reaction was incubated at 37° C. for 30 min, and then heated at 95° C. for 10 min to inactivate the λ-exonuclease. The single-stranded p8-L1 fragments were extracted successively with phenol, phenol-chloroform and chloroform, purified by ultrafiltration using a moistened Amicon-30 filter and resuspended in water. The concentration of purified p8-L1 driver DNA was measured at $A_{260nm}$ and adjusted to 0.5 μg/μL. Similarly, single-stranded driver DNA was prepared for 12S rRNA using the plasmid p8-12S and the teaching of this example.

EXAMPLE 13

Effect of Dimethyl Sulfoxide (DMSO) Concentration on Subtractive Amplification The tester RNA transcripts for the P3-adapted p7-L1 and the P3-adapted p7λ43, p7λ99 and p7λ260 mixture were diluted as required in water. Three first-round standard hybridization reactions were prepared following the teaching of Example 3, but with the following changes: (1) DTT and Hybridase™ were not included; (2) DMSO was added to reactions #1, #2 and #3 to final concentrations (v/v) of 35%, 40% and 45%, respectively; (3) the driver DNA in each reaction comprised single-stranded DNA from the plasmids p8-L1 (0.4 pmol) and p8-12S (1 pmol), both generated using lambda exonuclease as set forth Example 12, and 20 pmol each of the oligonucleotides OGS 54 (SEQ. ID. NO. 32), OGS 55 (SEQ. ID. NO. 33) and OGS 56 (SEQ. ID. NO. 29); (4) the tester RNA in each reaction comprised P3-adapted p7-L1 RNA (6 fmol) and the P3adapted p7λ(43, 99,260) RNA mixture (0.17 amol); and (5) the reaction volume was reduced to 20 μL. The components of the hybridization reactions were assembled at room temperature and hybridization performed according to Program C:3 (Ericomp TwinBlock™ System; Ericomp Inc.) comprising 65° C. for 10 min, 63° C. for 10 min, 61° C. for 15 min, 59° C. for 20 min, 57° C. for 30 min, 55° C. for 60 min, 53° C. for 90 min, 51° C. for 90 min, 49° C. for 120 min, 47° C. for 120 min, 45° C. for 120 min, 42.5° C. for 150 min and 40° C. for 180 min.

Following hybridization, reactions #1, #2 and #3 were diluted in water by 30%, 40% and 50%, respectively, in a total volume of 10 μL for each. Each reaction was then incubated at 37° C. for 60 minutes with 1.25 μL of a mixture containing 0.5 unit E. coli RNase H (Pharmacia), 36.4 mM $MgCl_2$ and 10 mM DTT. Next, 9.75 μL $H_2O$ was added to each reaction followed by 2 μL of a mixture containing 1 unit DNase I (Promega) and 45 mM $MgCl_2$. The reactions were incubated at 37° C. for a further 60 min.

Next, standard RT-PCR reactions were prepared following the teaching of Example 11 with the exception that Primer 3 was used instead of Primer 2, both in the reverse transcriptase reaction and in PCR. The amplification was performed for 14 cycles using the same thermocycling profile as taught by Example 3. A 5-μL aliquot of each PCR reaction was removed and placed immediately on ice.

Finally, RNA was synthesized from the amplified DNA by adding 2.5-μL of the PCR reaction to a standard transcription reaction containing 50 mM TrisHCl (pH 8.5), 50 mM KCl, 8 mM $MgCl_2$, 1.5 mM ATP, 1.5 mM GTP, 1.5 mM CTP, 1.5 mM UTP, 10 mM DTT and 60 units T7 RNA polymerase in a final volume of 20 μL. After incubating the reactions at 37° C. for 30 min, 1 μL (1 unit) DNase I was added to each and incubation continued at 37° C. for another 30 min, followed by 65° C. for 5 min.

Second-round hybridization reactions were assembled similar to the first-round hybridization reactions (#1, #2 and #3) except that the tester RNA for each comprised a 2-μL aliquot of a $10^{-2}$ dilution of the corresponding first-round transcription reaction. Thereafter, all ensuing steps with regards to the treatment of the second-round hybridization reactions were similar to those done for the first-round hybridization reactions, including transcription of the DNA amplified in the second round of PCR.

Third-round hybridization reactions were assembled similar to the second-round hybridization reactions except that the RNA synthesized in the second round transcription reaction was used as tester RNA. Once again, the ensuing steps with regards to the treatment of the third-round hybridization reactions were similar to those done for the first-round hybridization reactions, except that PCR was continued for 32 cycles and there was no transcription reaction.

The DNA amplified in each of the third-round PCR reactions was cloned and analyzed by colony-blot hybridization. The amplified DNA was first purified using QIAquick columns (QIAGEN catalog #28104) to remove primers and incomplete products from the PCR reactions. The purified DNA was then digested with Mlu I and Sau3A I and ligated into the Mlu I and BamH I sites of pSL1190 (Pharmacia), which was used to transform *E. coli*. Transformant colonies were transferred to filter paper (Whatman catalog #1541-090), lysed in denaturing solution (1.5 M NaCl; 0.5 M NaOH) for 7 min, and then soaked in neutralizing solution (1.5 M NaCl; 0.5 M Tris-HCl (pH 7.5); 0.001 M EDTA). After fixing under UV light for 2 min, the filters were hybridized with radiolabeled probes for the lambda subclones as set forth in Table 6 (OGS-31, SEQ. ID. NO. 34; OGS-32, SEQ. ID. NO. 35; OGS44, SEQ. ID. NO. 36), and mRNA encoding actin and glyceraldehyde-3-phosphate dehydrogenase (G3PDH) as set forth in Table 6 (OGS-35, SEQ. ID. NO. 37; OGS43, SEQ. ID. NO. 38), according to the teaching of Example 3. Hybridization was performed at 50° C. for 16 h. Filters were washed in 0.1 ×SSC- 0.5% SDS for 15 min, dried and then exposed to X-ray film. The radiolabeled signals for each probe were counted and those numbers were compared with the total number of colonies counted on a plate representing the transformation.

The initial amount of target sequences in the tester RNA mixture was measured by mixing 6 fmol P3adapted p7-L1 RNA with 1.7 amol P3-adapted p7λ(43,99,260) RNA mixture, and amplifying the resulting RNA mixture with RT-PCR following the teaching of this example for the third round. The amplified DNA was then cloned and analyzed by colony-blot hybridization, as set forth in this example.

The results of colony-blot hybridization of cloned DNA products from the tester RNA mixtures are presented in Table 7. Amplification of the tester RNA mixture with RT-PCR alone, i.e. without hybridization to the driver DNA, confirms that λ43 sequences were present in the initial tester RNA mixture at a level of 0.006% of the total. After three rounds of subtractive amplification the λ43 sequences were enriched from this initial level by 100 to 200 fold to final levels of 0.6% to 1.2% of the total. The enrichment of λ43 was optimum under hybridization conditions including 40% DMSO. Moderate enrichment of λ43 was observed with 35% DMSO, but this hybridization condition was less effective in inactivating other sequences in the tester RNA mixture, such as the abundant sequences derived from actin and G3PDH. Relative to one of these abundant sequences, the λ43 sequence was enriched by as much as 16000 fold under the hybridization conditions with 40% DMSO.

Example 14

Effect of PCR Between Rounds of Subtraction Amplification and Effect of Sorbitol or Trehalose in the Hybridization Reaction Three standard first-round hybridization reactions similar to reaction #2 (40% DMSO) of Example 13 were prepared, except that reactions #2 and #3 contained 2 µL of 2 M trehalose and 2 µL of 5 M sorbitol, respectively. The ensuing hybridization, RNase H and DNase I reactions were performed following the teaching of Example 13. Aliquots of each reaction were added to standard cDNA synthesis reactions that were assembled and performed following the teaching of Example 13. However, instead of PCR being performed next, a DNA conversion reaction was performed, in which the cDNA was extended using a promoter template to append a T7 promoter. The promoter template that was used was an oligonucleotide of the same sequence as Primer 1, but was blocked at its 3'-end with an amino group. The cDNA synthesis reactions were incubated at 65° C. for 10 min, followed by the addition 1 µL (1.25 pmol) of Primer 1 to each. The reactions were then heated at 94° C. for 90 seconds and cooled to 50° C. before 1 µL (5 units) AMV reverse transcriptase was added to each reaction. The reactions were incubated at 50° C. for 45 min and then 65° C. for 15 min. Finally, RNA was synthesized by adding a 10-µL aliquot of each DNA conversion reaction to standard transcription reactions, which were assembled and performed following the teaching of Example 13.

Second-round hybridization reactions were assembled similar to the first-round hybridization reactions except that the tester for each comprised a 2-µL aliquot of the corresponding first-round transcription reaction. Thereafter, all ensuing steps with regards to the treatment of the second-round hybridization reactions were similar to those done for the first-round hybridization reactions, including cDNA synthesis, DNA conversion using the promoter template and transcription.

Third-round hybridization reactions were assembled similar to the second-round hybridization reactions except that the RNA synthesized in the second-round transcription reaction was used as tester RNA. However, the treatment of the third-round hybridization reactions was the same as that for the third-round hybridization following the teaching of Example 13, including the performance of standard RT-PCR for 40 cycles. The amplified DNA for each third-round PCR reaction was cloned and analyzed by colony-blot hybridization, following the teaching of Example 13.

The results of colony-blot hybridization of cloned DNA products from the tester RNA mixtures are presented in Table 8. By not using PCR between rounds of subtractive amplification, the level of enrichment of the λ43 sequence rose to 23% of the total mixture of cloned sequences, a 3800-fold enrichment (reaction #1). In comparing the results with those of Table 7 (reaction #2), the procedure of this example was 19 times more effective for enrichment of λ43 than the one involving PCR in each round as set forth in Example 13. However, a second sequence λ99, which was initially present in the same tester RNA mixture at a level comparable to that of λ43, was enriched only 10 fold. One explanation of the apparent loss of λ99 relative to λ43 sequences could be in chemical instability of RNA under the hybridization conditions, which would have a greater effect on longer RNA species. Including either trehalose or sorbitol in the hybridization conditions (reactions #2 and #3, respectively) significantly improved the enrichment of λ99 to levels of 2.8% and 4.3%, respectively. As expected, the level of enrichment of the λ43 sequence was lower (17% and 16%, respectively) under hybridization conditions that would diminish the non-specific loss of the longer RNA species in the tester RNA mixture. Similar to what was observed with reaction #2 of Example 13, all of the hybridization conditions were effective in inactivating the other sequences in the tester RNA mixture, such as the abundant sequences derived from actin and G3PDH mRNA. Relative to one of these abundant sequences, the λ43 and λ99 sequences were enriched by as much as $2\times10^6$ and $5\times10^5$ fold, respectively.

Although preferred embodiments of the invention have been described in detail, it will be understood by those skilled in the art that variations may be made thereto without departing from either the spirit of the invention or the scope of the appended claims.

TABLE 1

| Sequence I.D. No. | Sequence (5' → 3') | Description |
|---|---|---|
| 3 | AAA AAT GCA TTG GAG TGC GGG CAC ATC AGT GT | gcsfrfwd.pcr |
| 4 | TTT CAA GCT TAG GCA TGC GTT CTC AGC TCC AGG CT | gcsfrrev.pcr |
| 5 | AAA ATG CAT CGC AAG ATG TCT CCT TGC TGG CA | mplfwd1a.pcr |
| 6 | AGA AGA AGC CTT GGG AGC TA | mplrev1a.pcr |
| 7 | CAA TGG CAG CAA CAG GAC CA | mplfwd2a.pcr |
| 8 | AAA AAG CTT CAG CTC GAG GAG GCG GTC TCG GTG GCG GTC T | mplrev2a.pcr |

TABLE 2

| Sequence I.D. No. | Sequence (5' → 3') | Description |
|---|---|---|
| 9 | TCG AGC TAG CGG CCG CAT AGT AAT GCA TAG ATC TCC AGT GAT TTT TTT CTC CAT CTC CCT ATA GTG AGT CGT ATT AG | catcon1 |
| 10 | GAT CTA TGC ATT ACT ATG CGG CCG CTA GCT CGA GTG ATA ATA AGC GGA TGA ATG GCT GCA | catcon2 |
| 11 | AAT TCT AAT ACG ACT CAC TAT AGG GAG ATG GAG AAA AAA ATC ACT GGA | Primer 1 (P1) |
| 12 | GCC ATT CAT CCG CTT ATT ATC AC | Primer 2 (P2) |
| 13 | CGC GTG GCG CGC CAT TAA TTA ATG CGG CCG | OGS-3 |
| 14 | CTA GCG GCC GCA TTA ATT AAT GGC GCG CCA CGC GTC CAG TGA TTT TTT TCT CCA TCT CCC TAT AGT GAG TCG TAT TAG | OGS-9 |
| 19 | CTG GGT CCC ATC AGA CAG ACG CTG CTG C | G-CSFR |
| 20 | CTG CAT CTC CAG GCA GGT CCA CAG TCA C | c-mpl |
| 21 | GAT CGT GAT AAT AAG CG | OGS-12 |
| 22 | TGA TGT GCC CGC ACT CCA ATG CAC GCG | OGS-15 |
| 23 | AGC AAG GAG ACA TCT TGC GAT GCA GCG | OGS-16 |

TABLE 3

| Sequence I.D. No. | Sequence (5' → 3') | Description |
|---|---|---|
| 15 | GGGAGATGGA GAAAAAAATC ACTGGAGATC TATGCAGCCA TCTGGACCCG GAGCCACAGA TTCTGTGGAG ACTGGGAGCA GAGCTTCAGC CCGGGGGCAG GCAGCAGCGT CTGTCTGATG GGACCCAGGA ATCTATCATC ACCCTGCCCC ACCTCAACCA CACTCAGGGG CTAGCTCGAG TGATAATAAG CGGATGAATG GC | P3-G RNA |
| 16 | GCCATTCATC CGCTTATTAT CACTCGAGCT AGCCCCTGAG TGTGGTTGAG GTGGGGCAGG GTGATGATAG ATTCCTGGGT CCCATCAGAC AGACGCTGCT GCCTGCCCCC GGGCTGAAGC TCTGCTCCCA GTCTCCACAG AATCTGTGGC TCCGGGTCCA GATGGCTGCA TAGATCTCCA GTGATTTTTT TCTCCATCTC CC | P3-G cDNA |
| 17 | GGGAGATGGA GAAAAAAATC ACTGGAGATC TATGCAGCTG CGCAGCGAAC CTGATGGGAT CTCCCTCGGT GGCTCCTGGG GATCCTGGTC CCTCCCTGTG ACTGTGGACC TGCCTGGAGA TGCAGTGGCA CTTGACTGCA ATGCTTTAC CTTGGACCTG AAGAATGTTA CCTGTCAATG GCAGCAACAG GACCATGCTA GCTCGAGTGA TAATAAGCGG ATGAATGGC | P4-M RNA |
| 18 | GCCATTCATC CGCTTATTAT CACTCGAGCT AGCATGGTCC TGTTGCTGCC ATTGACAGGT AACATTCTTC AGGTCCAAGG TAAAGCATTG CAGTCCAAGT GCCACTGCAT CTCCAGGCAG GTCCACAGTC ACAGGGAGGG ACCAGGATCC CCAGGAGCCA CCGAGGGAGA TCCCATCAGG TTCGCTGCGC AGCTGCATAG ATCTCCAGTG ATTTTTTTT CCATCTCCC | PR-M cDNA |

TABLE 4

Effect of RNase H

| | Fold Enrichment of Target | | Ratio |
|---|---|---|---|
| Method | (−RNase H) | (+RNase H) | (+RNase H):(−RNase H) |
| RT-PCR | 5.53 | 16.16 | 2.92 |
| NASBA | 7.20 | 32.05 | 4.45 |

TABLE 5

| Sequence I.D. No. | Sequence (5' → 3') | Description |
|---|---|---|
| 24 | GGGAGATGGA GAAAAAAATC ACTGGACGCG TGCATTGGAG TGCGGGCACA TCAGTGTCTC AGCCCCCATC GTCCACCTGG GGGATCGTGA TAATAAGCGG ATGAATGGC | P5-G RNA |
| 25 | GGGAGATGGA GAAAAAAATC ACTGGACGCG TGCATCGCAA GATGTCTCCT TGCTGGCATC AGACTCAGAG CCCCTGAAGT GTTTCTCCCG AACATTTGAG GACCTCACTT GCTTCTGGGA TGAGGAAGAG GCAGCGCCCA GTGGGACATA CCAGCTGCTG TATGCCTACC CGCGGGAGAA GCCCCGTGCT TGCCCCCTGA GTTCCCAGAG CATGCCCCAC TTTGGAACCC GATACGTGTG CCAGTTTCCA GACCAGGAGG AAGTGCGTCT CTTCTTTCCG CTGCACCTCT GGGTGAAGAA TGTGTTCCTA AACCAGACTC GGACTCAGCG AGTCCTCTTT GTGGACAGTG TAGGCCTGCC GGCTCCCCCC AGTATCATCA AGGCCATGGG TGGGAGCCAG CCAGGGGAAC TTCAGATCGT GATAATAAGC GGATGAATGG C | P6-M RNA |
| 26 | GCCATTCATC CGCTTATTAT CACGATCCCC CAGGTGGACG ATGGGGGCTG AGACACTGAT GTGCCCGCAC TCCAATGCAC GCGTCCAGTG ATTTTTTTCT CCATCTCCC | P5-G cDNA |
| 27 | GCCATTCATC CGCTTATTAT CACGATCTGA AGTTCCCCTG GCTGGCTCCC ACCCATGGCC TTGATGATAC TGGGGGGAGC CGGCAGGCCT ACACTGTCCA CAAAGAGGAC TCGCTGAGTC CGAGTCTGGT TTAGGAACAC ATTCTTCACC CAGAGGTGCA GCGGAAAGAA GAGACGCACT TCCTCCTGGT CTGGAAACTG GCACACGTAT CGGGTTCCAA AGTGGGGCAT GCTCTGGGAA CTCAGGGGGC AAGCACGGGG CTTCTCCCGC GGGTAGGCAT ACAGCAGCTG GTATGTCCCA CTGGGCGCTG CCTCTTCCTC ATCCCAGAAG CAAGTGAGGT CCTCAAATGT TCGGAGAAA CACTTCAGGG GCTCTGAGTC TGATGCCAGC AAGGAGACAT CTTGCGATGC ACGCGTCCAG TGATTTTTTT CTCCATCTCC C | P6-M cDNA |

TABLE 6

| Sequence I.D. No. | Sequence (5' → 3') | Description |
|---|---|---|
| 28 | AAC CCT GCG GCC GCT TTT TTT TTT TV | VdT$_{11}$Not1 |
| 29 | TGA ACT CAC TGG AAC GGG GAT GCT | OGS-56* |
| 30 | GCC TGC ACC AAC AGT TAA CA | Primer 3 (P3) |
| 31 | GAT CTG TTA ACT GTT GGT | P3 Adaptor |
| 32 | AAG TAG GAG AGG AGC GAG CGA CCA AAG GAA | OGS-54* |
| 33 | GCC CGA GGT TAT CTA GAG TCA CCA AAG CCG | OGS-55* |
| 34 | AGG AGG CTC ACG GAC GCG AAG AAC A | OGS-31 |
| 35 | CTG CGC GCC TGT GCA CTC TGT GGT G | OGS-32 |
| 36 | GAA AGC CAG AAC TCC CCG TAT ACA GAC A | OGS-44 |
| 37 | TGC TCA ATG GGG TAC TTC AGG GTC AGG AT | OGS-35 |
| 38 | CAT TGA TGA CAA GCT TCC CGT TCT CA | QGS-43 |

*These oligos were synthesized blocked and unblocked on their 3' ends.

TABLE 7

| Experimental Condition (DMSO Concentration) | Relative Number of Colonies Hybridizing to Each Sequence (Probe) | | |
|---|---|---|---|
| | λ43 (OGS-31) | actin (OGS-43) | G3PDH (OGS-35) |
| No Hybridization Reaction | 0.006% | 0.29% | 1.61% |
| Subtractive Amplification #1 (35% DMSO) | 1.0% | 0.1% | 0.3% |
| Subtractive Amplification #2 (40% DMSO) | 1.2% | <0.02% | <0.02% |
| Subtractive Amplification #3 (45% DMSO) | 0.6% | <0.02% | <0.02% |

TABLE 8

| Experimental Condition (Additive) | Relative Number of Colonies Hybridizing to Each Sequence (Probe) | | | |
|---|---|---|---|---|
| | λ43 (OGS-31) | λ99 (OGS-32) | actin (OGS-43) | G3PDH (OGS-35) |
| No Hybridization Reaction | 0.006% | 0.007% | 0.29% | 1.61% |
| Subtractive Amplification #1 | 23% | 0.07% | <0.002% | <0.002% |
| Subtractive Amplification #2 | 17% | 2.8% | <0.002% | <0.002% |
| Subtractive Amplification #3 | 16% | 4.3% | <0.002% | <0.002% |

What is claimed is:

1. A kit for preferentially amplifying target RNA in a sample of tester RNA relative to non-target RNA in the sample, the kit containing:

driver nucleic acid sequences complementary to the non-target tester RNA under conditions where the driver sequences hybridize to the non-target RNA;

a nucleic acid primer capable of hybridizing to the target RNA under conditions suitable for extension of the nucleic acid primer; and a promoter template capable of hybridizing to a DNA that is complementary to the target RNA under conditions suitable for extension of the complementary DNA such that a functional double stranded promoter is formed.

2. The kit according to claim 1 wherein the nucleic acid primer is DNA.

3. The kit according to claim 1 wherein the promoter template is DNA.

4. The kit according to claim 3 wherein the promoter template includes sequences capable of forming a biologically-active promoter and transcription initiation site from a bacteriophage.

5. The kit according to claim 4 wherein the bacteriophage is T7.

6. The kit according to claim 1 further including a reverse transcriptase.

7. The kit according to claim 1 further including a ribonuclease.

8. The kit according to claim 7 wherein the ribonuclease is ribonuclease H.

9. The kit according to claim 1 further including a DNA polymerase.

10. The kit according to claim 1 further including a RNA polymerase.

11. The kit according to claim 1 further including organic and inorganic chemicals necessary to establish reaction conditions that enable subtractive amplification.

* * * * *

SEQUENCE LISTING

<160> NUMBER OF SEQ ID NOS: 38

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
taatacgact cactata                                                  17

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
aattctaata cgactcacta tagggaga                                      28

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
aaaaatgcat tggagtgcgg gcacatcagt gt                                 32

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
tttcaagctt aggcatgcgt tctcagctcc aggct                              35

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
aaaatgcatc gcaagatgtc tccttgctgg ca                                 32

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
agaagaagcc ttgggagcta                                          20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
caatggcagc aacaggacca                                          20

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
aaaaagcttc agctcgagga ggcggtctcg gtggcggtct                    40

<210> SEQ ID NO 9
<211> LENGTH: 77
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tcgagctagc ggccgcatag taatgcatag atctccagtg attttttct ccatctccct   60 atagtgagtc gtattag                                             77

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gatctatgca ttactatgcg gccgctagct cgagtgataa taagcggatg aatggctgca   60

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
aattctaata cgactcacta tagggagatg gagaaaaaaa tcactgga        48

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 12
gccattcatc cgcttattat cac                                              23

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
cgcgtggcgc gccattaatt aatgcggccg                                       30

<210> SEQ ID NO 14
<211> LENGTH: 78
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ctagcggccg cattaattaa tggcgcgcca cgcgtccagt gattttttc tccatctccc        60 tatagtgagt cgtattag                                                    78

<210> SEQ ID NO 15
<211> LENGTH: 202
<212> TYPE: DNA
<213> ORGANISM: Homo sapiens

<400> SEQUENCE: 15
gggagatgga gaaaaaaatc actggagatc tatgcagcca tctggacccg gagccacaga       60
ttctgtggag actgggagca gagcttcagc ccggggcag gcagcagcgt ctgtctgatg       120
ggacccagga atctatcatc accctgcccc acctcaacca cactcagggg ctagctcgag      180
tgataataag cggatgaatg gc                                              202

<210> SEQ ID NO 16
<211> LENGTH: 202
<212> TYPE: DNA
<213> ORGANISM: Homo sapiens

<400> SEQUENCE: 16
gccattcatc cgcttattat cactcgagct agcccctgag tgtggttgag gtgggcagg        60 gtgatgatag attcctgggt cccatcagac agacgctgct gcctgccccc gggctgaagc      120
tctgctccca gtctccacag aatctgtggc tccgggtcca gatggctgca tagatctcca     180 gtgattttt tctccatctc cc                                              202

<210> SEQ ID NO 17
<211> LENGTH: 229
<212> TYPE: DNA
<213> ORGANISM: Homo sapiens

<400> SEQUENCE: 17
gggagatgga gaaaaaaatc actggagatc tatgcagctg cgcagcgaac ctgatgggat       60
ctccctcggt ggctcctggg gatcctggtc cctccctgtg actgtggacc tgcctggaga     120
tgcagtggca cttggactgc aatgctttac cttggacctg aagaatgtta cctgtcaatg     180
gcagcaacag gaccatgcta gctcgagtga taataagcgg atgaatggc                 229
```

<210> SEQ ID NO 18
<211> LENGTH: 229
<212> TYPE: DNA
<213> ORGANISM: Homo sapiens

<400> SEQUENCE: 18
gccattcatc cgcttattat cactcgagct agcatggtcc tgttgctgcc attgacaggt    60
aacattcttc aggtccaagg taaagcattg cagtccaagt gccactgcat ctccaggcag   120
gtccacagtc acagggaggg accaggatcc ccaggagcca ccgagggaga tcccatcagg   180
ttcgctgcgc agctgcatag atctccagtg attttttct ccatctccc                229

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ctgggtccca tcagacagac gctgctgc                                        28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ctgcatctcc aggcaggtcc acagtcac                                        28

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gatcgtgata ataagcg                                                    17

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
agcaaggaga catcttgcga tgcagcg                                         27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23

```
agcaaggaga catcttgcga tgcagcg                                              27

<210> SEQ ID NO 24
<211> LENGTH: 109
<212> TYPE: DNA
<213> ORGANISM: Homo sapiens

<400> SEQUENCE: 24
gggagatgga gaaaaaaatc actggacgcg tgcattggag tgcgggcaca tcagtgtctc          60
agcccccatc gtccacctgg gggatcgtga taataagcgg atgaatggc                    109

<210> SEQ ID NO 25
<211> LENGTH: 441
<212> TYPE: DNA
<213> ORGANISM: Homo sapiens

<400> SEQUENCE: 25
gggagatgga gaaaaaaatc actggacgcg tgcatcgcaa gatgtctcct tgctggcatc          60
agactcagag cccctgaagt gtttctcccg aacatttgag gacctcactt gcttctggga        120
tgaggaagag gcagcgccca gtgggacata ccagctgctg tatgcctacc gcgggagaa         180 gccccgtgct tgcccctga gttcccagag catgccccac tttggaaccc gatacgtgtg        240
ccagtttcca gaccaggagg aagtgcgtct cttctttccg ctgcacctct gggtgaagaa        300
tgtgttccta aaccagactc ggactcagcg agtcctcttt gtggacagtg taggcctgcc        360
ggctcccccc agtatcatca aggccatggg tgggagccag ccaggggaac ttcagatcgt        420
gataataagc ggatgaatgg c                                                 441

<210> SEQ ID NO 26
<211> LENGTH: 109
<212> TYPE: DNA
<213> ORGANISM: Homo sapiens

<400> SEQUENCE: 26
gccattcatc cgcttattat cacgatcccc caggtggacg atgggggctg agacactgat         60
gtgcccgcac tccaatgcac gcgtccagtg attttttttct ccatctccc                   109

<210> SEQ ID NO 27
<211> LENGTH: 441
<212> TYPE: DNA
<213> ORGANISM: Homo sapiens

<400> SEQUENCE: 27
gccattcatc cgcttattat cacgatctga agttcccctg gctggctccc acccatggcc         60
ttgatgatac tgggggagc cggcaggcct acactgtcca caaagaggac tcgctgagtc        120
cgagtctggt ttaggaacac attcttcacc cagaggtgca gcgaaagaa gagacgcact        180 tcctcctggt ctggaaactg gcacacgtat cgggttccaa agtggggcat gctctgggaa        240 ctcaggggc aagcacgggg cttctcccgc gggtaggcat acagcagctg gtatgtccca        300
ctgggcgctg cctcttcctc atcccagaag caagtgaggt cctcaaatgt tcgggagaaa        360
cacttcaggg gctctgagtc tgatgccagc aaggagacat cttgcgatgc acgcgtccag        420
tgattttttt ctccatctcc c                                                 441

<210> SEQ ID NO 28
<211> LENGTH: 26
<212> TYPE: DNA
```

<213> ORGANISM: Artificial Sequence
<220> FEATURE:
<223> OTHER INFORMATION: Description of Artificial Sequence: Synthetic
      Primer

<400> SEQUENCE: 28
aaccctgcgg ccgctttttt tttttv                                          26

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
tgaactcact ggaacgggga tgct                                            24

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
gcctgcacca acagttaaca                                                 20

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
gatctgttaa ctgttggt                                                   18

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
aagtaggaga ggagcgagcg accaaaggaa                                      30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
gcccgaggtt atctagagtc accaaagccg                                      30

<210> SEQ ID NO 34
<211> LENGTH: 25
<212> TYPE: DNA
<213> ORGANISM: Artificial Sequence

```
<220> FEATURE:
<223> OTHER INFORMATION: Description of Artificial Sequence: Synthetic
      Primer

<400> SEQUENCE: 34
aggaggctca cggacgcgaa gaaca                                            25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
ctgcgcgcct gtgcactctg tggtg                                            25

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
gaaagccaga actccccgta tacagaca                                         28

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
tgctcaatgg ggtacttcag ggtcaggat                                        29

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
cattgatgac aagcttcccg ttctca                                           26
```